United States Patent [19]

Takaya et al.

[11] Patent Number: 4,761,410
[45] Date of Patent: Aug. 2, 1988

[54] CEPHEM COMPOUNDS

[75] Inventors: Takao Takaya; Kazuo Sakane; Kenzi Miyai, all of Kawanishi; Teruaki Matuo, Ibaraki, all of Japan

[73] Assignee: Fujisawa Pharmaceutical Co., Ltd., Osaka, Japan

[21] Appl. No.: 815,015

[22] Filed: Dec. 31, 1985

[30] Foreign Application Priority Data

Jan. 14, 1985 [GB] United Kingdom ................. 8500807
Jun. 24, 1985 [GB] United Kingdom ................. 8515910

[51] Int. Cl.$^4$ ................. C07D 501/38; A61K 31/545
[52] U.S. Cl. ................................ 514/206; 540/225; 540/227
[58] Field of Search ................. 540/225, 227; 514/206

[56] References Cited

U.S. PATENT DOCUMENTS 4,328,225  5/1982  Vignau et al.
4,593,022  6/1986  Labeeuw ............................ 540/225

FOREIGN PATENT DOCUMENTS 2039890  8/1980  United Kingdom .

Primary Examiner—Nicholas S. Rizzo
Attorney, Agent, or Firm—Oblon, Fisher, Spivak, McClelland & Maier

[57] ABSTRACT

The invention relates to antimicrobial compounds of the formula:

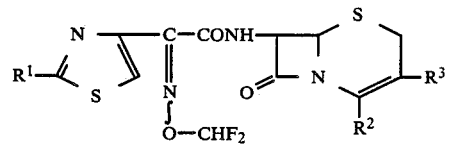

wherein
  $R^1$ is amino or a protected amino group,
  $R^2$ is carboxy or a protected carboxy group and
  $R^3$ is thiadiazolylthiomethyl or thiadiazolylthiomethyl substituted with lower alkyl, and pharmaceutically acceptable salts thereof.

8 Claims, No Drawings

CEPHEM COMPOUNDS

The present invention relates to new cephem compounds and pharmaceutically acceptable salts thereof. More particularly, it relates to new cephem compounds and pharmaceutically acceptable salts thereof, which have antimicrobial activities and to processes for preparation thereof, to pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compound is novel and can be represented by the following general formula (I).

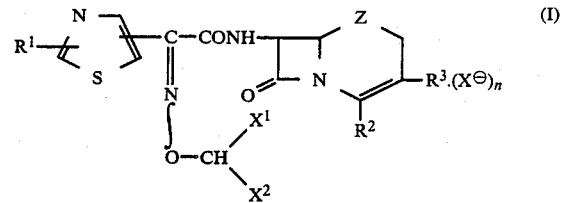

wherein
$R^1$ is amino or a protected amino group,
$R^2$ is carboxy, $-COO^\ominus$ or a protected carboxy group,
$R^3$ is heterocyclicthiomethyl which may be substituted with suitable substituent(s), halomethyl, cyanovinylthiomethyl, carbamoyloxymethyl, pyridiniomethyl substituted with 1 to 3 substituent(s) selected from the group consisting of lower alkyl, lower alkylthio, lower alkoxy, hydroxy(lower)alkyl and lower alkanesulfonyl, vinyl, hydrogen, pyridiniothiomethyl having lower alkyl, pyridylthiovinyl, pyridiniothiovinyl having lower alkyl, pyrrolidiniomethyl having lower alkyl, hydroxymethyl, tetrahydropyridylmethyl or tetrahydroisoquinolylmethyl,
Z is $-S-$ or

X is an acid residue,
n is 0 or 1,
$X^1$ is halogen and
$X^2$ is halogen.

According to the present invention, the object compounds (I) can be prepared by the following processes.

Process 1

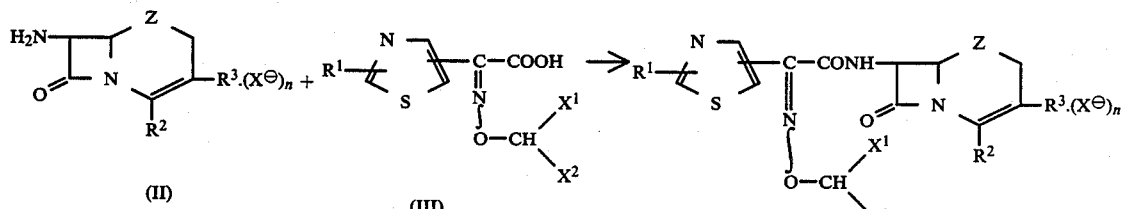

(II)
or its reactive derivative at the amino group or a salt thereof (III)
or its reactive derivative at the carboxy group or a salt thereof (I)
or a salt thereof Process 2

Elimination reaction of the amino protective group

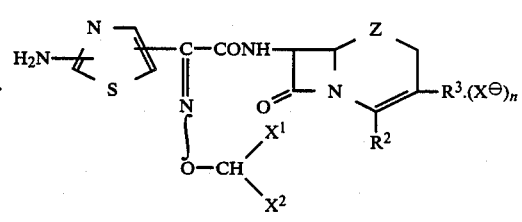

(Ia)
or a salt thereof (Ib)
or a salt thereof

-continued
Process 3
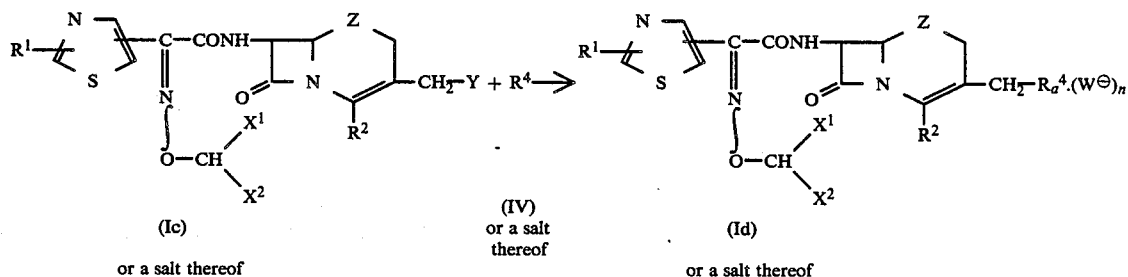
(Ic) or a salt thereof
(IV) or a salt thereof
(Id) or a salt thereof
Process 4
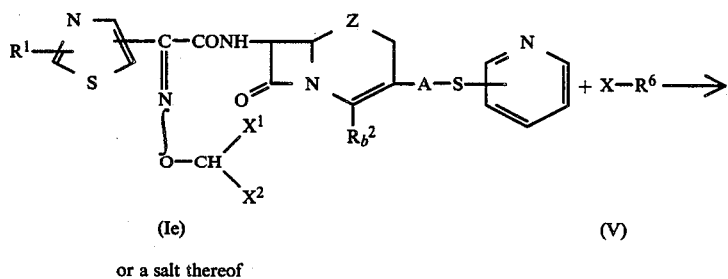
(Ie) or a salt thereof
(V)
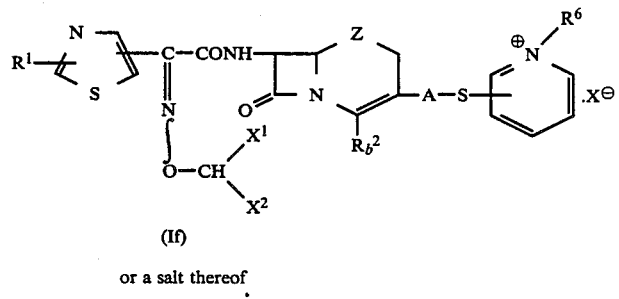
(If) or a salt thereof
Process 5
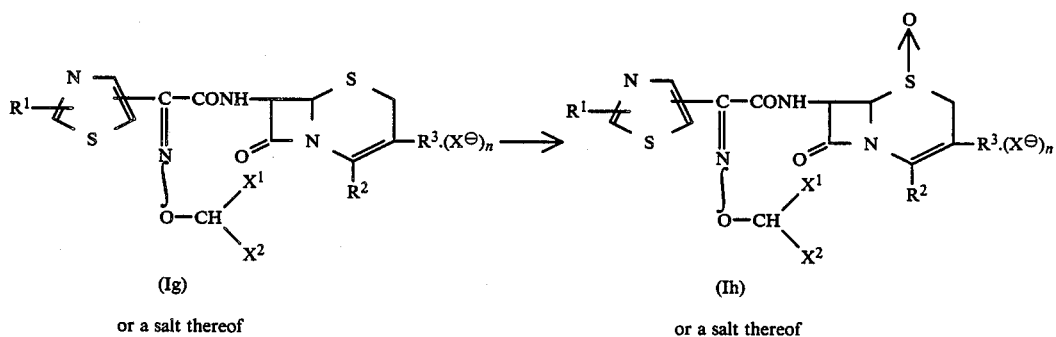
(Ig) or a salt thereof
(Ih) or a salt thereof
Process 6

<chemical structure>
(Ih) or a salt thereof
</chemical structure>

<chemical structure>
(Ig) or a salt thereof
</chemical structure> wherein
 R$^1$, R$^2$, R$^3$, Z, X, n, X$^1$ and X$^2$ are each as defined above,
 R$_a^1$ is a protected amino group,
 Y is an acid residue,
 R$^4$ is pyridine substituted with 1 to 3 substituent(s) selected from the group consisting of lower alkyl, lower alkylthio, lower alkoxy, hydroxy(lower)alkyl and lower alkanesulfonyl, pyrrolidine having lower alkyl, tetrahydropyridine, tetrahydroisoquinoline,
 or a compound of the formula: H—S—R$^5$.(X$^\ominus$)$_n$
 wherein
  X and n are each as defined above, and
  R$^5$ is heterocyclic group which may be substituted with suitable substituent(s), cyanovinyl or pyridinio having lower alkyl,
 R$_a^4$ is pyridinio substituted with 1 to 3 substituent(s) selected from the group consisting of lower alkyl, lower alkylthio, lower alkoxy, hydroxy(lower)alkyl and lower alkanesulfonyl, pyrrolidinio having lower alkyl, tetrahydropyridyl, tetrahydroisoquinolyl,
 or a group of the formula: —S—R$^5$ wherein R$^5$ is as defined above,
 W is Y as defined above or X as defined above,
 R$_b^2$ is carboxy or a protected carboxy group,
 A is —CH$_2$— or —CH=CH—, and
 R$^6$ is lower alkyl.

Some of the starting compounds (II) are novel and can be prepared by the following Process (A).

Process A:

<chemical structure>
(IIa) or a salt thereof + (IVa) or a salt thereof →

(IIb) or a salt thereof
</chemical structure> wherein
 R$_b^2$ and Y are each as defined above,
 R$_b^4$ is 1,2,5-thiadiazole-3-thiol or 1,2,4-thiadiazole-5-thiol, and
 R$_c^4$ is (1,2,5-thiadiazol-3-yl)thio group or (1,2,4-thiadiazol-5-yl)thio group.

The reaction conditions of Process A can be referred to the ones of Preparations 4 and 5.

Regarding the compounds (I), (Ia), (Ib), (Ic), (Id), (Ie), (If), (Ig), (Ih) and (III), it is to be understood that said compounds include syn isomer, anti isomer and a mixture thereof.

For example, with regard to the object compound (I), syn isomer means one geometrical isomer having the partial structure represented by the following formula:

<chemical structure syn isomer>

(wherein R$^1$, X$^1$ and X$^2$ are each as defined above) and anti isomer means the other geometrical isomer having the partial structure represented by the following formula:

<chemical structure anti isomer>

(wherein R$^1$, X$^1$ and X$^2$ are each as defined above.)

Suitable pharmaceutically acceptable salts of the object compounds (I) are conventional non-toxic salts and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, etc.), an inorganic acid salt (e.g. hydrochloride, hydrobromide, sulfate, phosphate, etc.), a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in detail as follows.

The term "lower" is intended to mean 1 to 6 carbon atoms, unless otherwise indicated.

Suitable "protected amino" may include an acylamino or an amino group substituted by a conventional protecting group such as ar(lower)alkyl which may have at least one suitable substituent(s), (e.g. benzyl, trityl, etc.) or the like.

Suitable acyl moiety in the term "acylamino" may include aliphatic acyl group and acyl group containing an aromatic or heterocyclic ring. And, suitable examples of the said acyl may be lower alkanoyl (e.g. formyl, acetyl, propionyl, butyryl, isobutyryl, valeryl, isovaleryl, oxalyl, succinyl, pivaloyl, etc.); lower alkoxycarbonyl (e.g. methoxycarbonyl, ethoxycarbonyl, propoxycarbonyl, 1-cyclopropylethoxycarbonyl, isopropoxycarbonyl, butoxycarbonyl, tert-butoxycarbonyl, pentyloxycarbonyl, hexyloxycarbonyl, etc.);

lower alkanesulfonyl (e.g. mesyl, ethanesulfonyl, propanesulfonyl, isopropanesulfonyl, butanesulfonyl, etc.);

arenesulfonyl (e.g. benzenesulfonyl, tosyl, etc.); aroyl (e.g. benzoyl, toluoyl, xyloxy, naphthoyl, phthaloyl, indancarbonyl, etc.); ar(lower)alkanoyl (e.g. phenylacetyl, phenylpropionyl, etc.);

ar(lower)alkoxycarbonyl (e.g. benzyloxycarbonyl, phenethyloxycarbonyl, etc.), and the like. The acyl moiety as stated above may have at least one suitable substituent(s) such as halogen (chlorine, bromine, fluorine and iodine) or the like.

Suitable "protected carboxy" may include an esterified carboxy and the like, and suitable examples of the ester moiety in said esterified carboxy may be the ones such as lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester, etc.) which may have at least one suitable substituent(s), for example, lower alkanoyloxy(lower)alkyl ester (e.g. acetoxymethyl ester, propionyloxymethyl ester, butyryloxymethyl ester, valeryloxymethyl ester, pivaloyloxymethyl ester, 2-acetoxyethyl ester, 2-propionyloxyethyl ester, hexanoyloxymethyl ester, etc.), lower alkanesulfonyl(lower)alkyl ester (e.g. 2-mesylethyl ester, etc.) or mono(or di or tri)halo(lower)alkyl ester (e.g. 2-iodoethyl ester, 2,2,2-trichloroethyl ester, etc.); lower alkenyl ester (e.g. vinyl ester, allyl ester, etc.); lower alkynyl ester (e.g. ethynyl ester, propynyl ester, etc.);

ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.); aryl ester which may have at least one suitable substituent(s) (e.g. phenyl ester, 4-chlorophenyl ester, tolyl ester, tert-butylphenyl ester, xylyl ester, mesityl ester, cumenyl ester, etc.), and the like.

Suitable heterocyclic group and heterocyclic moiety in the term "heterocyclicthiomethyl" means saturated or unsaturated, monocyclic or polycyclic heterocyclic group containing at least one hetero-atom such as an oxygen, sulfur, nitrogen atom and the like. And, especially preferably heterocyclic group may be heterocyclic group such as unsaturated 3 to 8-membered heteromonocyclic group containing 1 to 4 nitrogen atom(s), for example, pyrrolyl, pyrrolinyl, imidazolyl, pyrazolyl, pyridyl, and its N-oxide, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl (e.g., 4,5-dihydro-1,2,4-triazinyl, 2,5-dihydro-1,2,4-triazinyl, etc.), etc.;

saturated 3 to 8-membered heteromonocyclic group containing 1 to 4 nitrogen atom(s), for example, pyrrolidinyl, imidazolidinyl, piperidino, piperazinyl, etc.;

unsaturated condensed heterocyclic group containing 1 to 5 nitrogen atom(s), for example, indolyl, isoindolyl, indolizynyl, benzimidazolyl, quinolyl, isoquinolyl, indazolyl, benzotriazolyl, tetrazolopyridyl, tetrazolopyridazinyl (e.g., tetrazolo[1,5-b]pyridazinyl, etc.), dihydrotriazolopyridazinyl, etc.;

unsaturated 3 to 8-membered heteromonocyclic group containing 1 to 2 oxygen atom(s) and 1 to 3 nitrogen atom(s), for example, oxazolyl, isoxazolyl, oxadiazolyl, (e.g., 1,2,4-oxadiazolyl, 1,3,4-oxadiazolyl, 1,2,5-oxadiazolyl, etc.), etc.;

saturated 3 to 8-membered heteromonocyclic group containing 1 to 2 oxygen atom(s) and 1 to 3 nitrogen atom(s), for example, morpholinyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered heteromonocyclic group containing 1 to 2 sulfur atom(s) and 1 to 3 nitrogen atom(s), for example, 1,3-thiazolyl, 1,2-thiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl), etc.;

saturated 3 to 8-membered heteromonocyclic group containing 1 to 2 sulfur atom(s) and 1 to 3 nitrogen atom(s), for example, thiazolidinyl, etc.;

unsaturated 3 to 8-membered heteromonocyclic group containing a sulfur atom, for example, thienyl, etc.; unsaturated condensed heterocyclic group containing 1 to 2 sulfur atom(s) and 1 to 3 nitrogen atom(s), for example, benzothiazolyl, benzothiadiazolyl, etc. and the like;

wherein said heterocyclic group may be substituted with 1 to 3 suitable substituent(s) such as lower alkyl (e.g., methyl, ethyl, propyl, isopropyl, butyl, isobutyl, pentyl, cyclopentyl, hexyl, cyclohexyl, etc.);

lower alkylthio (e.g., methylthio, ethylthio, propylthio, etc.); lower alkenyl (e.g., vinyl, allyl, butenyl, etc.);

lower alkenylthio (e.g., vinylthio, allylthio, butenylthio, etc.); hydroxy; aryl (e.g., phenyl, tolyl, etc.); halogen (e.g., chlorine, bromine, iodine or fluorine); amino; di(lower)alkylamino(lower)alkyl (e.g., dimethylaminomethyl, dimethylaminoethyl, dimethylaminopropyl, diethylaminopropyl, diethylaminobutyl, etc.); carboxy(lower)alkyl (e.g., carboxymethyl, carboxyethyl, carboxypropyl, etc.); esterified carboxy(lower)alkyl wherein the esterified carboxy moiety is exemplified above;

amino(lower)alkyl (e.g., aminomethyl, aminoethyl, aminopropyl, 1-aminomethylethyl, aminobutyl, aminohexyl, etc.), protected amino(lower)alkyl wherein the protected amino and lower alkyl moieties are each as exemplified above, preferably lower alkoxycarbonylamino(lower)alkyl (e.g., methoxycarbonylaminomethyl, ethoxycarbonylaminomethyl, t-butoxycarbonylaminomethyl, t-butoxycarbonylaminoethyl, t-butoxycarbonylaminopropyl, etc.) or lower alkanoylamino(lower)alkyl (e.g., acetylaminomethyl, acetylaminoethyl, acetylaminopropyl, 1-acetylaminomethylethyl, etc.); carboxy; oxo;

esterified carboxy as exemplified above, preferably lower alkoxycarbonyl; lower alkoxy(lower)alkyl (e.g., methoxymethyl, methoxyethyl, methoxypropyl, ethoxymethyl, ethoxyethyl, etc.); hydroxy(lower)alkyl (e.g., hydroxymethyl, hydroxyethyl, hydroxypropyl, hydroxybutyl, etc.); lower alkylthio(lower)alkyl (e.g., methylthiomethyl, methylthioethyl, methylthiopropyl, ethylthiomethyl, etc.); sulfo(lower)alkyl (e.g., sulfomethyl, sulfoethyl, sulfopropyl, sulfobutyl, etc.); lower alkanesulfonyl (e.g., mesyl, ethanesulfonyl, propanesulfonyl, butanesulfonyl, etc.);

acyl(lower)alkyl wherein the acyl and lower alkyl moieties are each as exemplified above, preferably lower alkanesulfonyl(lower)alkyl (e.g., mesylmethyl, mesylethyl, ethanesulfonylmethyl, etc.);

acylamino(lower)alkyl wherein the acyl and lower alkyl moieties are each as exemplified above, preferably lower alkanesulfonylamino(lower)alkyl (e.g. mesylaminomethyl, mesylaminoethyl, mesylaminopropyl, ethanesulfonylaminomethyl, etc.); carboxy(lower)alkylthio (e.g., carboxymethylthio, carboxyethylthio, etc.); morpholino(lower)alkyl (e.g., morpholinomethyl, morpholinoethyl, morpholinopropyl, etc.); piperidino(lower)alkyl (e.g., piperidinomethyl, piperidinoethyl, piperidinopropyl, etc.);

piperazinyl(lower)alkyl which may be substituted with lower alkyl (e.g., 4-methyl-1-piperazinylpropyl, etc.); or the like.

Suitable halomethyl may include chloromethyl, bromomethyl, fluoromethyl and iodomethyl.

Suitable "lower alkyl" may include methyl, ethyl, propyl, isopropyl, butyl, isobutyl, t-butyl, pentyl, t-pentyl, hexyl and the like.

Suitable "lower alkylthio" may include methylthio, ethylthio, propylthio, butylthio, pentylthio, hexylthio and the like.

Suitable "lower alkoxy" may include methoxy, ethoxy, propoxy, isopropoxy, butoxy, t-butoxy, pentyloxy, hexyloxy and the like.

Suitable "hydroxy(lower)alkyl" may include hydroxymethyl, 1(or 2)-hydroxyethyl, 1(or 2 or 3)-hydroxypropyl, 1(or 2 or 3 or 4)-hydroxybutyl, 1(or 2 or 3 or 4 or 5)-hydroxypentyl, 1(or 2 or 3 or 4 or 5 or 6)-hydroxyhexyl and the like.

Suitable "lower alkanesulfonyl" may include mesyl, ethanesulfonyl, propanesulfonyl, butanesulfonyl, pentanesulfonyl, hexanesulfonyl and the like.

Suitable "halogen" may include chlorine, bromine, fluorine and iodine, and preferred one is fluorine.

Suitable "acid residue" may include acyloxy, halogen (e.g., fluorine, chlorine, bromine or iodine) and the like, wherein acyl moiety in the term "acyloxy" can be referred to the ones as exemplified above.

Preferred embodiments of the object compounds (I) are as follows.

Preferred embodiment of $R^1$ is amino or ar(lower)alkylamino (more preferably triphenyl(lower)alkylamino, most preferably tritylamino), $R^2$ is carboxy, —COO⊖ or esterified carboxy(more preferably ar-(lower)alkoxycarbonyl, most preferably benzhydryloxycarbonyl), $R^3$ is thiadiazolylthiomethyl (more preferably 1,3,4-thiadiazolylthiomethyl, 1,2,4-thiadiazolylthiomethyl, 1,2,5-thiadiazolylthiomethyl or 1,2,3-thiadiazolylthiomethyl), thiadiazolylthiomethyl substituted with lower alkyl (more preferably 1,2,4-thiadiazolylthiomethyl substituted with lower alkyl, or 1,3,4-thiadiazolylthiomethyl substituted with lower alkyl), thiazolylthiomethyl substituted with hydroxy and carboxy (more preferably 1,2-thiazolylthiomethyl substituted with hydroxy and carboxy), tetrazolylthiomethyl substituted with lower alkyl, tetrazolylthiomethyl substituted with di(lower)alkylamino(lower)alkyl, tetrazolylthiomethyl substituted with hydroxy(lower)alkyl, dihydrotriazinylthiomethyl substituted with oxo, hydroxy and lower alkyl (more preferably 4,5-dihydro-1,2,4-triazinylthiomethyl substituted with oxo, hydroxy and lower alkyl, or 2,5-dihydro-1,2,4-triazinylthiomethyl substituted with oxo, hydroxy and lower alkyl), tetrazolopyridazinylthiomethyl (more preferably tetrazolo[1,5-b]pyridazinylthiomethyl), halomethyl, cyanovinylthiomethyl, carbamoyloxymethyl, pyridiniomethyl substituted with two lower alkyl groups, pyridiniomethyl substituted with hydroxy(lower)alkyl, pyridiniomethyl substituted with lower alkyl, pyridiniomethyl substituted with lower alkoxy, pyridiniomethyl substituted with lower alkylthio, pyridiniomethyl substituted with lower alkanesulfonyl, vinyl, hydrogen, pyridiniothiomethyl having lower alkyl, pyridylthiovinyl, pyridiniothiovinyl having lower alkyl, pyrrolidiniomethyl having lower alkyl, hydroxymethyl, tetrahydropyridylmethyl or tetrahydroisoquinolylmethyl, Z is —S— or

X is an acid residue (more preferably halogen, or mono(or di or tri)halo(lower)alkanoyloxy, n is 0 or 1, $X^1$ is halogen (more preferably fluorine) and $X^2$ is halogen (more preferably fluorine).

The processes for preparing the object compounds of the present invention are explained in detail in the following.

Process 1

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as N,O-bis(trimethylsilyl)acetamide, N-trimethylsilylacetamide or the like; a derivative formed by the reaction of the compound (II) with phosphorus trichloride or phosgene, and the like.

Suitable salts of the compounds (II) and (III) can be referred to the ones as exemplified for the compound (I).

Suitable reactive derivative at the carboxy group of the compound (III) may include an acid halide, an acid anhydride, an activated amide, an activated ester, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfonic acid (e.g. methanesulfonic acid, ethanesulfonic acid, etc.), sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (III) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling or at ambient temperature.

Process 2

The object compound (Ib) or a salt thereof can be prepared by subjecting the compound (Ia) or a salt thereof to elimination reaction of the amino protective group.

Suitable salts of the compounds (Ia) and (Ib) can be referred to the ones as exemplified for the compound (I).

The elimination reaction is carried out in accordance with a conventional method such as hydrolysis; reduction; a method treating the compound (Ia) wherein protected amino of $R_a^1$ is acylamino with iminohalogenating agent, iminoetherifying agent and then, if necessary, hydrolyzing the resultant; or the like. The hydrolysis may include a method using an acid or base or hydrazine and the like. These methods may be selected depending on the kind of the protective groups to be eliminated.

Among these methods, hydrolysis using an acid is one of the most common and preferable method for eliminating the protective groups such as substituted or unsubstituted alkoxycarbonyl, for example, tert-pentyloxycarbonyl, lower alkanoyl (e.g. formyl, acetyl, etc.), cycloalkoxycarbonyl, substituted or unsubstituted aralkoxycarbonyl, aralkyl (e.g. trityl), substituted phenylthio, substituted aralkylidene, substituted alkylidene, substituted cycloalkylidene or the like.

Suitable acid includes an organic or inorganic acid such as formic acid, trifluoroacetic acid, benzenesulfonic acid, p-toluenesulfonic acid, hydrochloric acid and the like, and the most suitable acid is an acid which can easily be removed from the reaction mixture by a conventional manner such as distillation under reduced pressure, for example, formic acid, trifluoroacetic acid, hydrochloric acid, etc. The acids can be selected according to the kind of the protective group to be eliminated. When the elimination reaction is conducted with an acid, it can be carried out in the presence or absence of a solvent.

Suitable solvent includes water, methylene chloride, alcohol (e.g., methanol, ethanol, etc.), tetrahydrofuran or any other organic solvents which do not adversely influence the reaction, or a mixture thereof.

The elimination reaction using trifluoroacetic acid may be carried out in the presence of anisole. The hydrolysis using hydrazine is commonly applied for eliminating a phthaloyl, succinyl type amino-protective group.

The elimination using base is used for eliminating an acyl group such as trifluoroacetyl. Suitable base may include an inorganic base and an organic base.

The reductive elimination is generally applied for eliminating the protective group, for example, haloalkoxycarbonyl (e.g. trichloroethoxycarbonyl, etc.), substituted or unsubstituted aralkoxycarbonyl (e.g. benzyloxycarbonyl, etc.), 2-pyridylmethoxycarbonyl, etc. Suitable reduction may include, for example, reduction with an alkali metal borohydride (e.g. sodium borohydride, etc.), reduction with a combination of a metal (e.g. tin, zinc, iron, etc.) or the said metal together with a metal salt compound (e.g. chromous chloride, chromous acetate, etc.) and an organic or inorganic acid (e.g. acetic acid, propionic acid, hydrochloric acid, etc.); and catalytic reduction. Suitable catalyst includes a conventional one, for example, Raney nickel, platinum oxide, palladium on carbon and the like.

Among the protective groups, the acyl group can generally be eliminated by hydrolysis. Especially, halogen substituted-alkoxycarbonyl and 8-quinolyloxycarbonyl groups are usually eliminated by treating with a heavy metal such as copper, zinc, or the like.

Among the protective groups, the acyl group can also be eliminated by treating with an iminohalogenating agent (e.g. phosphorus oxychloride, etc.) and an iminoetherifying agent such as lower alkanol (e.g. methanol, ethanol, etc.), if necessary, followed by hydrolysis.

The reaction temperature is not critical and may suitably be selected in accordance with the kind of the amino protective group and the elimination method as mentioned above, and the reaction is usually carried out under a mild condition such as under cooling or at slightly elevated temperature.

The present invention includes, within its scope, the case that the protected carboxy group for $R^2$ is transformed into the free carboxy group in the course of the elimination reaction as mentioned above or in the post-treatment of the reaction mixture or reaction product.

Process 3

The object compound (Id) or a salt thereof can be prepared by reacting the compound (Ic) or a salt thereof with the compound (IV) or a salt thereof.

Suitable salt of the compound (Ic) can be referred to the ones as exemplified for the compound (I).

Suitable salt of the compound (IV) may include a metal salt such as an alkali metal salt (e.g., sodium salt, potassium salt, etc.), silver salt or the like.

The present reaction may be carried out in a solvent such as water, phosphate buffer, acetone, chloroform, nitrobenzene, methylene chloride, ethylene chloride, acetonitrile, N,N-dimethylformamide, methanol, ethanol, ether, tetrahydrofuran, dimethylsulfoxide, or any other organic solvent which does not adversely affect the reaction, preferably in ones having strong polarities. Among the solvents, hydrophilic solvents may be used in a mixture with water. The reaction is preferably carried out in around neutral medium. When the compound (IV) is used in a free form, the reaction is preferably conducted in the presence of a base, for example, inorganic base such as alkali metal hydroxide, alkali metal carbonate, alkali metal bicarbonate, organic base such as trialkylamine, and the like. The reaction temperature is not critical, and the reaction is usually carried out under cooling, at ambient temperature, under warming or under heating.

Process 4

The object compound (If) or a salt thereof can be prepared by reacting the compound (Ie) or a salt thereof with the compound (V).

Suitable salts of the compounds (Ie) and (If) can be referred to the ones as exemplified for the compound (I).

The reaction is usually carried out in a solvent such as water, acetone, tetrahydrofuran, ethanol, ether, N,N-dimethylformamide or any other solvent which does not adversely influence the reaction.

The reaction temperature is not critical and the reaction is usually carried out under cooling to heating.

Process 5

The object compound (Ih) or a salt-thereof can be prepared by oxidizing the compound (Ig) or a salt thereof.

Suitable salts of the compounds (Ig) and (Ih) can be referred to the ones as exemplified for the compound (I).

The oxidizing agent to be used in this reaction may include an inorganic peracid or a salt thereof (e.g. periodic acid, persulfuric acid, or sodium or potassium salt thereof, etc.), an organic peracid or a salt thereof (e.g. perbenzoic acid, m-chloroperbenzoic acid, performic acid, peracetic acid, chloroperacetic acid, trifluoroperacetic acid, or sodium or potassium salt thereof, etc.), ozone, hydrogen peroxide, urea-hydrogen peroxide, or any other conventional oxidizing agent which can oxidize a thio group to a sulfinyl group.

The present oxidation reaction is usually carried out in a conventional solvent which does not adversely influence the reaction such as water, acetic acid, chloroform, methylene chloride, acetone, methanol, ethyl acetate, ethanol or a mixture thereof.

The reaction temperature is not critical and the reaction is preferably carried out from under cooling to at ambient temperature.

Process 6

The object compound (Ig) or a salt thereof can be prepared by reducing the compound (Ih) or a salt thereof.

The present reduction can be carried out by a conventional method which is applied for the transformation of

into —S—, for example, by using phosphorus trichloride, a combination of stannous chloride and acetyl chloride, a combination of an alkali metal iodide (e.g. sodium iodide, etc.) and trihaloacetic anhydride (e.g. trifluoroacetic anhydride, etc.), and the like.

The present reduction is usually carried out in a solvent such as acetone, dioxane, acetonitrile, N,N-dimethylformamide, benzene, hexane, chloroform, methylene chloride, ethylene chloride, tetrahydrofuran, ethyl acetate, or any other solvent which does not adversely affect the reaction.

The reaction temperature is not critical and the reaction is usually carried out under cooling or at ambient temperature.

The object compound (I) and pharmaceutically acceptable salt thereof of the present invention are novel compounds which exhibit high antibacterial activity and inhibit the growth of a wide variety of pathogenic microorganisms including Gram-positive and Gram-negative bacteria and are useful as anti-microbial agents. For therapeutic purpose, the compounds according to the present invention can be used in the form of pharmaceutical preparation which contain said compounds, as an active ingredient, in admixture with a pharmaceutically acceptable carrier such as an organic or inorganic solid or liquid excipient suitable for oral, parenteral or external administration. The pharmaceutical preparations may be capsules, tablets, dragees, ointments or suppositories, solutions, suspension, emulsions, and the like. If desired, there may be included in the above preparations auxiliary substances, stabilizing agents, wetting or emulsifying agents, buffers and other commonly used additives.

While the dosage of the compounds will vary depending upon the age and condition of the patient, an average single dose of about 10 mg, 50 mg, 100 mg, 0 mg, 500 mg and 1000 mg of the compounds according to the present invention was proved to be effective for treating infectious diseases caused by pathogenic bacteria. In general, amounts between 1 mg/body and about 6,000 mg/body or even more may be administered per day. In order to illustrate the usefulness of the object compound, anti-microbial activities of the representative compounds of the present invention are shown below.

[1] Test Compound (1) 7-[2-(2-Aminothiazol-4-yl)-2-difluoromethoxyiminoacetamido]-3-(3-methyl-1-pyridiniomethyl)-3-cephem-4-carboxylate (syn isomer) [hereinafter referred to as Test Compound (1)]

(2) 7-[2-(2-Aminothiazol-4-yl)-2-difluoromethoxyiminoacetamido]-3-(3-methyl-1,2,4-thiadiazol-5-yl)thiomethyl-3-cephem-4-carboxylic acid (syn isomer) [hereinafter referred to as Test Compound (2)]

(3) 7-[2-(2-Aminothiazol-4-yl)-2-difluoromethoxyiminoacetamido]-3-(1,2,4-thiadiazol-5-yl)thiomethyl-3-cephem-4-carboxylic acid (syn isomer) [hereinafter referred to as Test Compound (3)]

Test Method

In vitro antibacterial activity was determined by the two-fold agar-plate dilution method as described below.

One loopful of an overnight culture of each test strain in Trypticase-soy broth ($10^8$ viable cells per ml) was streaked on heart infusion agar HI-agar) containing graded concentrations of representative test compound, and the minimal inhibitory concentration (MIC) was expressed in terms of $\mu$g/ml after incubation at 37° C. for 20 hours.

[3] Test Results

| | MIC ($\mu$g/ml) | | |
| --- | --- | --- | --- |
| | Test compound | | |
| Test strains | (1) | (2) | (3) |
| Escherichia coli 29 | ≦0.025 | 0.200 | 0.100 |
| Proteus vulgaris IAM 1025 | ≦0.025 | 0.050 | ≦0.025 |

The following Preparations and Examples are given for the purpose of illustrating the present invention.

Preparation 1

To an ice-cooled solution of propiolamide (1 g) in tetrahydrofuran (10 ml) and water (10 ml) was added a mixture of triphenylmethanethiol (4.2 g), tetrahydrofuran (10 ml) and 1N aqueous solution (1 ml) of sodium hydroxide at 0°–5° C. The mixture was stirred for 30 minutes at 0°–10° C. To the reaction mixture was added water (40 ml) and the mixture was cooled. The resultant precipitates were collected by filtration to give (Z)-3-tritylthioacrylamide (4.2 g).

IR (Nujol): 3380, 3180, 1640, 1570 cm$^{-1}$

Preparation 2

To an ice-cooled suspension of (Z)-3-tritylthioacrylamide (3.9 g) in N,N-dimethylformamide (40 ml) was added phosphorus pentachloride (3.65 g) and the mixture was stirred for 30 minutes at 20° C. The reaction mixture was poured into ice-water and extracted with ethyl acetate. The separated organic layer was washed with brine, dried over magnesium sulfate and evaporated in vacuo to give (Z)-3-tritylthioacrylonitrile (2.85 g).

IR (Nujol): 2200 cm$^{-1}$

NMR (DMSO-d$_6$, $\delta$): 5.65 (1H, d, J=10 Hz), 6.88 (1H, d, J=10 Hz), 7–7.67 (15H, m)

Preparation 3

To a solution of (Z)-3-tritylthioacrylonitrile (3.5 g) in a mixture of tetrahydrofuran (14 ml), methanol (21 ml) and pyridine (0.9 ml) was dropwise added a solution of silver nitrate (2.26 mg) in a mixture of methanol (55 ml) and water (5.5 ml) at ambient temperature. The reaction mixture was stirred at 40° C. in dark. The precipitate was collected, washed with methanol and dried over phosphorus pentoxide to give [(Z)-2-cyanovinylthio]silver (2.46 g).

IR (Nujol): 2200, 1530 cm$^{-1}$

Preparation 4

7-Aminocephalosporanic acid (0.272 g) was added to the solution of potassium 1,2,5-thiadiazole-3-thiolate (0.136 g) in trifluoroacetic acid (5 ml) and the mixture was stirred for a few minutes until the solution turned clear, and then, boron trifluoride etherate (0.434 g) was added thereto and the mixture was stirred for 12 hours at room temperature. The reaction mixture was evaporated under reduced pressure and the residue was adjusted to pH 3.0 with 2% aqueous solution of ammonium hydroxide. The precipitates were collected by filtration, washed with cool water, acetone and diethyl ether and dried to give 7-amino-3-(1,2,5-thiadiazol-3-yl)thiomethyl-3-cephem-4-carboxylic acid (0.210 g).

IR (Nujol): 3150, 1800, 1620, 1530 cm$^{-1}$

NMR (CF$_3$COOH, $\delta$): 3.87 (2H, s), 4.41, 4.93 (2H, ABq, J=14 Hz), 5.33 (2H, m), 8.57 (1H, s)

Preparation 5

7-Aminocephalosporanic acid (21.2 g) was added to the solution of potassium 1,2,4-thiadiazole-5-thiolate (10.6 g) in trifluoroacetic acid (370 ml) and the mixture was stirred for a few minutes until the solution turned clear, and then, boron trifluoride etherate (33.8 g) was added thereto and the mixture was stirred for 7 hours at room temperature. The reaction mixture was evaporated under reduced pressure and the residue was adjusted to pH 3.0 with 3% aqueous soltuion of ammonium hydroxide. The precipitates were collected by filtration, washed with acetone and diethyl ether and dried to give a crude object compound (28.5 g). The crude object compound (25.0 g) was suspended in concentrated hydrochloric acid (230 ml), and the mixture was stirred for 30 minutes at room temperature. After insoluble material was removed by filtration, the solution was adjusted to pH 3.0 with 28% aqueous solution of ammonium hydroxide under ice-cooling. The resulting precipitates were collected by filtration, washed with cool water, acetone and diisopropyl ether and dried to give 7-amino-3-(1,2,4-thiadiazol-5-yl)thiomethyl-3-cephem-4-carboxylic acid (15.8 g).

IR (Nujol): 3150, 1790, 1610, 1530 cm$^{-1}$

NMR (CF$_3$COOH, $\delta$): 3.87 (2H, s), 4.63, 4.97 (2H, ABq, J=14 Hz), 5.43 (2H, m), 8.93 (1H, s)

Example 1

To a solution of 2-(2-tritylaminothiazol-4-yl)-2-difluoromethoxyiminoacetic acid (syn isomer) (0.8 g) and diisopropylethylamine (0.43 g) in N,N-dimethylformamide (20 ml) was added mesyl chloride (0.38 g) at −20° C. and the mixture was stirred at the same temperature for 30 minutes to give an activated acid solution. To a solution of 7-amino-3-(1,3,4-thiadiazol-2-yl)thiomethyl- 3-cephem-4-carboxylic acid (0.57 g) and N-trimethylsilylacetamide (1.8 g) in tetrahydrofuran (20 ml) was added the activated acid solution obtained above all at once at −10° C. After being stirred at the same temperature for an hour, the mixture was poured into water and adjusted to pH 2.5 with an aqueous solution of sodium bicarbonate. The precipitates were collected by filtration and washed with water to give 7-[2-(2-tritylaminothiazol-4-yl)-2-difluoromethoxyiminoacetamido]-3-(1,3,4-thiadiazol-2-yl)thiomethyl-3-cephem-4-carboxylic acid (syn isomer) (1.1 g).

IR (Nujol): 3250, 1780, 1680, 1530 cm$^{-1}$

NMR (DMSO-d$_6$, δ): 3.52, 3.79 (2H, ABq, J=18 Hz), 4.25, 4.58 (2H, ABq, J=14 Hz), 5.12 (1H, d, J=5 Hz), 5.67 (1H, dd, J=5 Hz, 8 Hz), 6.94 (1H, s), 7.03 (1H, t, J=72 Hz), 7.10–7.50 (15H, m), 8.89 (1H, broad s), 9.50 (1H, s), 9.80 (1H, d, J=8 Hz)

EXAMPLE 2

A mixture of 2-(2-tritylaminothiazol-4-yl)-2-difluoromethoxyiminoacetic acid (syn isomer) (2.4 g) and diisopropylethylamine (1.29 g) in N,N-dimethylformamide (35 ml) was cooled to −30° C. and mesyl chloride (1.15 g) was added dropwise thereto. The mixture was stirred at −20° to −30° C. for 30 minutes to give an activated acid solution. On the other hand, a mixture of benzhydryl 7-amino-3-chloromethyl-3-cephem-4-carboxylate (2.18 g) and N-trimethylsilylacetamide (5.25 g) in methylene chloride (20 ml) was stirred to be a clear solution for 30 minutes at room temperature and then cooled to −20° C. To this solution was added the activated acid solution obtained above in one portion. The mixture was stirred for 30 minutes at −15° to −10° C., poured into water and extracted with ethyl acetate. The extract was washed with water three times, dried over magnesium sulfate and evaporated under reduced pressure. The residue was triturated in diisopropyl ether to give benzhydryl 7-[2-(2-tritylaminothiazol-4-yl)-2-difluoromethoxyiminoacetamido]-3-chloromethyl-3-cephem-4-carboxylate (syn isomer) (4.64 g).

IR (Nujol): 1780, 1720, 1670, 1590, 1520 cm$^{-1}$

EXAMPLE 3

To a solution of 2-(2-tritylaminothiazol-4-yl)-2-difluoromethoxyiminoacetic acid (syn isomer) (1.3 g) and diisopropylethylamine (0.7 g) in N,N-dimethylformamide (20 ml) was added mesyl chloride (0.62 g) at −20° C.

The mixture was stirred at the same temperature for 30 minutes and added dropwise to a solution of 7-amino-3-(1,2,3-thiadiazol-5-yl)thiomethyl-3-cephem-4-carboxylic acid (0.9 g) and sodium bicarbonate (0.46 g) in a mixture of tetrahydrofuran (15 ml) and water (15 ml) at 0° to 5° C. while keeping the pH value at 7.5 to 8.0 with 5% aqueous solution of sodium bicarbonate. The solution was stirred for 30 minutes at 0° to 5° C., adjusted to pH 7.5 and poured into water (300 ml). The resultant precipitates were collected by filtration, washed with water and dried to give 7-[2-(2-tritylaminothiazol-4-yl)-2-difluoromethoxyiminoacetamido]-3-(1,2,3-thiadiazol-5-yl)thiomethyl-3-cephem-4-carboxylic acid (syn iscmer) (1.78 g).

IR (Nujol): 3200, 1780, 1680, 1520 cm$^{-1}$

NMR (DMSO-d$_6$, δ): 3.60 (2H, broad s), 4.23 (2H, broad s), 5.13 (1H, d, J=5 Hz), 5.65 (1H, dd, J=5 Hz, 8 Hz), 6.92 (1H, s), 7.00 (1H, t, J=72 Hz), 7.00–7.50 (15H, m), 8.80 (1H, s), 8.80 (1H, broad s), 9.78 (1H, d, J=8 Hz)

EXAMPLE 4

The following compounds were obtained according to similar manners to those of Examples 1 to 3.

(1) 7-[2-(2-Aminothiazol-4-yl)-2-difluoromethoxyiminoacetamido]-3-(1,3,4-thiadiazol-2-yl)thiomethyl-3-cephem-4-carboxylic acid (syn isomer)

IR (Nujol): 3300, 1770, 1670, 1530 cm$^{-1}$ (2) Benzhydryl 7-[2-(2-tritylaminothiazol-4-yl)-2-difluoromethoxyiminoacetamido]-3-(4-methyl-5-oxo-6-hydroxy-4,5-dihydro-1,2,4-triazin-3-yl)thiomethyl-3-cephem-4-carboxylate (syn isomer)

IR (Nujol): 1780, 1705, 1670, 1580, 1520 cm$^{-1}$ (3) 7-[2-(2-Aminothiazol-4-yl)-2-difluoromethoxyiminoacetamido]-3-(4-methyl-5-oxo-6-hydroxy-4,5-dihydro-1,2,4-triazin-3-yl)thiomethyl-3-cephem-4-carboxylic acid (syn isomer)

IR (Nujol): 1770, 1690, 1680, 1580, 1520 cm$^{-1}$ (4) 7-[2-(2-Aminothiazol-4-yl)-2-difluoromethoxyiminoacetamido]-3-(1,2,3-thiadiazol-5-yl)thiomethyl-3-cephem-4-carboxylic acid (syn isomer)

IR (Nujol): 3250, 1770, 1670, 1620, 1530 cm$^{-1}$ (5) 7-[2-(2-Tritylaminothiazol-4-yl)-2-difluoromethoxyiminoacetamido]-3-(3-methyl-1-pyridiniomethyl)-3-cephem-4-carboxylate (syn isomer)

IR (Nujol): 3300, 1780, 1670, 1620, 1530 cm$^{-1}$

NMR (DMSO-d$_6$, δ): 3.10–3.63 (2H, m), 5.05 (1H, d, J=5 Hz), 5.10–5.63 (2H, m), 5.75 (1H, dd, J=5 Hz, 8 Hz), 6.87 (1H, s), 6.97 (1H, t, J=72 Hz), 7.00–7.50 (15H, m), 7.63–8.50 (2H, m), 8.83 (1H, broad s), 9.08 (2H, broad s)

(6) 7-[2-(2-Aminothiazol-4-yl)-2-difluoromethoxyiminoacetamido]-3-(3-methyl-1-pyridiniomethyl)-3-cephem-4-carboxylate (syn isomer)

IR (Nujol): 3300, 3150, 1770, 1670, 1610, 1530 cm$^{-1}$

7-[2-(2-Tritylaminothiazol-4-yl)-2-difluoromethoxyiminoacetamido]-3-[1-(2-hydroxyethyl)-1H-tetrazol-5-yl]thiomethyl-3-cephem-4-carboxylic acid (syn isomer)

IR (Nujol): 3230, 1780, 1680, 1530 cm$^{-1}$

NMR (DMSO-d$_6$, δ): 3.53, 3.90 (2H, ABq, J=18 Hz), 3.74 (2H, t, J=5 Hz), 4.20, 4.45 (2H, ABq, J=14 Hz), 4.25 (2H, t, J=5 Hz), 5.08 (1H, d, J=5 Hz), 5.66 (1H, dd, J=5 Hz, 8 Hz), 6.93 (1H, s), 7.02 (1H, t, J=72 Hz), 7.10–7.47 (15H, m), 8.90 (1H, broad s), 9.80 (1H, d, J=8 Hz)

(8) 7-[2-(2-Aminothiazol-4-yl)-2-difluoromethoxyiminoacetamido]-3-[1-(2-hydroxyethyl)-1H-tetrazol-5-yl]thiomethyl-3-cephem-4-carboxylic acid (syn isomer)

IR (Nujol): 3300, 1770, 1670, 1620, 1530 cm$^{-1}$ (9) 7-[2-(2-Tritylaminothiazol-4-yl)-2-difluoromethoxyiminoacetamido]-3-(1,2,4-thiadiazol-5-yl)thiomethyl-3-cephem-4-carboxylic acid (syn isomer)

IR (Nujol): 3300, 1780, 1650, 1590, 1530 cm$^{-1}$

NMR (DMSO-d$_6$, δ): 3.50–3.90 (2H, m), 4.30, 4.67 (2H, ABq, J=14 Hz), 5.13 (1H, d, J=5 Hz), 5.77 (1H, dd, J=5 Hz, 8 Hz), 6.90 (1H, s), 7.05 (1H, t, J=72 Hz), 7.00–7.57 (15H, m), 8.63 (1H, s), 8.85 (1H, broad s), 9.80 (1H, d, J=8 Hz)

(10) 7-[2-(2-Aminothiazol-4-yl)-2-difluoromethoxyiminoacetamido]-3-(1,2,4-thiadiazol-5-yl)thiomethyl-3-cephem-4-carboxylic acid (syn isomer)

IR (Nujol): 3250, 1770, 1670, 1620, 1530 cm$^{-1}$

(11) 7-[2-(2-Tritylaminothiazol-4-yl)-2-difluoromethoxyiminoacetamido]-3-[1-{2-(N,N-dimethylamino)ethyl}-1H-tetrazol-5-yl]thiomethyl-3-cephem-4-carboxylic acid (syn isomer)

IR (Nujol): 3250, 1770, 1660, 1530 cm$^{-1}$

NMR (DMSO-d$_6$, δ): 2.68 (3H, s), 2.83 (3H, s), 3.08 (2H, t, J=6 Hz), 3.43, 3.78 (2H, ABq, J=18 Hz), 4.53 (2H, t, J=6 Hz), 5.08 (1H, d, J=5 Hz), 5.63 (1H, dd,

J=5 Hz, 8 Hz), 6.95 (1H, s), 7.03 (1H, t, J=72 Hz), 7.10-7.50 (15H, m), 8.90 (1H, broad s), 9.83 (1H, d, J=8 Hz)

(12) 7-[2-(2-Aminothiazol-4-yl)-2-difluoromethoxyiminoacetamido]-3-[1-{2-(N,N-dimethylamino)ethyl}-1H-tetrazol-5-yl]thiomethyl-3-cephem-4-carboxylic acid (syn isomer)

IR (Nujol): 3300, 1670, 1610, 1530 cm$^{-1}$

(13) Benzhydryl 7-[2-(2-tritylaminothiazol-4-yl)-2-difluoromethoxyiminoacetamido]-3-[(Z)-2-cyanovinylthiomethyl]-3-cephem-4-carboxylate (syn isomer)

IR (Nujol): 3250, 2210, 1780, 1720, 1680, 1520, 1490 cm$^{-1}$

(14) 7-[2-(2-Aminothiazol-4-yl)-2-difluoromethoxyiminoacetamido]-3-[(Z)-2-cyanovinylthiomethyl]-3-cephem-4-carboxylic acid (syn isomer)

mp: 145° to 150° C. (dec.)

IR (Nujol): 3260, 2210, 1770, 1675, 1620, 1560 1530 cm$^{-1}$

(15) 7-[2-(2-Tritylaminothiazol-4-yl)-2-difluoromethoxyiminoacetamido]-3-(2-methyl-5-oxo-6-hydroxy-2,5-dihydro-1,2,4-triazin-3-yl)thiomethyl-3-cephem-4-carboxylic acid (syn isomer)

mp: 125° to 130° C. (dec.)

IR (Nujol): 3200, 1780, 1655, 1590, 1530 cm$^{-1}$

NMR (DMSO-d$_6$, δ): 3.60 (3H, s), 3.70 (2H, broad s), 4.10, 4.42 (2H, ABq, J=14 Hz), 5.15 (1H, d, J=5 Hz), 5.80 (1H, dd, J=5 Hz, 8 Hz), 6.97 (1H, s), 7.10 (1H, t, J=72 Hz), 7.15-7.50 (15H, m), 8.93 (1H, broad s), 9.83 (1H, d, J=8 Hz)

(16) 7-[2-(2-Aminothiazol-4-yl)-2-difluoromethoxyiminoacetamido]-3-(2-methyl-5-oxo-6-hydroxy-2,5-dihydro-1,2,4-triazin-3-yl)thiomethyl-3-cephem-4carboxylic acid (syn isomer)

mp: 165° to 170° C. (dec.)

IR (Nujol): 3300, 3200, 1780, 1680, 1640, 1530 cm$^{-1}$

(17) 7-[2-(2-Aminothiazol-4-yl)-2-difluoromethoxyiminoacetamido]-3-carbamoyloxymethyl-3-cephem-4-carboxylic acid (syn isomer)

mp: 125° to 130° C. (dec.)

IR (Nujol): 3450, 3350, 3260, 3200, 1770, 1720, 1680, 1650, 1600, 1530 cm$^{-1}$

(18) 7-[2-(2-Tritylaminothiazol-4-yl)-2-difluoromethoxyiminoacetamido]-3-carbamoyloxymethyl-3-cephem-4-carboxylic acid (syn isomer)

mp: 125° to 130° C. (dec.)

IR (Nujol): 3200, 1775, 1710, 1670, 1590, 1520 cm$^{-1}$

NMR (DMSO-d$_6$, δ): 3.57 (2H, broad s), 4.67, 4.90 (2H, ABq, J=14 Hz), 5.18 (1H, d, J=5 Hz), 5.77 (1H, dd, J=5 Hz, 8 Hz), 6.20-6.50 (2H), 6.97 (1H, s), 7.07 (1H, t, J=72 Hz), 7.20-7.50 (15H, m), 8.93 (1H, broad s), 9.83 (1H, d, J=8 Hz)

(19) 7-[2-(2-Aminothiazol-4-yl)-2-difluoromethoxyiminoacetamido]-3-(tetrazolo[1,5-b]pyridazin-6-yl)thiomethyl-3-cephem-4-carboxylic acid (syn isomer)

mp: 170° to 175° C. (dec.)

IR (Nujol): 3400, 3260, 3200, 1770, 1680, 1660, 1620, 1535 cm$^{-1}$

(20) 7-[2-(2-Tritylaminothiazol-4-yl)-2-difluoromethoxyiminoacetamido]-3-(tetrazolo[1,5-b]pyridazin-6-yl)thiomethyl-3-cephem-4-carboxylic acid (syn isomer)

mp: 130° to 135° C. (dec.)

IR (Nujol): 3200, 1785, 1680, 1595, 1575, 1530 cm$^{-1}$

NMR (DMSO-d$_6$, δ): 3.75 (2H, broad s), 4.28, 4.63 (2H, ABq, J=14 Hz), 5.20 (1H, d, J=5 Hz), 5.83 (1H, dd, J=5 Hz, 8 Hz), 7.03 (1H, s), 7.17 (1H, t, J=72 Hz), 7.20-7.50 (15H, m), 7.78 (1H, d, J=9 Hz), 8.63 (1H, d, J=9 Hz), 9.93 (1H, d, J=8 Hz)

(21) 7-[2-(2-Aminothiazol-4-yl)-2-difluoromethoxyiminoacetamido]-3-(1-methyl-1H-tetrazol-5-yl)thiomethyl-3-cephem-4-carboxylic acid (syn isomer)

mp: 145° to 150° C. (dec.)

IR (Nujol): 3300, 1770, 1670, 1620, 1530 cm$^{-1}$

(22) 7-[2-(2-Tritylaminothiazol-4-yl)-2-difluoromethoxyiminoacetamido]-3-(1-methyl-1H-tetrazol-5-yl)thiomethyl-3-cephem-4-carboxylic acid (syn isomer)

mp: 115° to 120° C. (dec.)

IR (Nujol): 3200, 1770, 1660, 1585, 1560, 1515 cm$^{-1}$

NMR (DMSO-d$_6$, δ): 3.68 (2H, broad s), 3.92 (3H, s), 4.30 (2H, broad s), 5.12 (1H, d, J=5 Hz), 5.75 (1H, dd, J=5 Hz, 8 Hz), 7.0 (1H, s), 7.10 (1H, t, J=72 Hz), 7.20-7.50 (15H, m), 8.70 (1H, broad s), 9.85 (1H, d, J=8 Hz)

(23) 7-[2-(2-Tritylaminothiazol-4-yl)-2-difluoromethoxyiminoacetamido]-3-vinyl-3-cephem-4-carboxylic acid (syn isomer)

mp: 105° to 110° C. (dec.)

IR (Nujol): 3200, 1770, 1680, 1650, 1585, 1565, 1520 cm$^{-1}$

NMR (DMSO-d$_6$, δ): 3.67 (2H, broad s), 5.20 (1H, d, J=5 Hz), 5.33 (1H, d, J=11 Hz), 5.58 (1H, d, J=17 Hz), 5.85 (1H, dd, J=5 Hz, 8 Hz), 7.00 (1H, dd, J=17 Hz, 11 Hz), 7.00 (1H, s), 7.10 (1H, t, J=72 Hz), 7.20-7.50 (15H, m), 9.93 (1H, d, J=8 Hz)

(24) 7-[2-(2-Aminothiazol-4-yl)-2-difluoromethoxyiminoacetamido]-3-vinyl-3-cephem-4-carboxylic acid (syn isomer)

mp: 190° to 195° C. (dec.)

IR (Nujol): 3420, 3320, 3250, 1770, 1670, 1615, 1530 cm$^{-1}$

(25) 7-[2-(2-Tritylaminothiazol-4-yl)-2-difluoromethoxyiminoacetamido]-3-(1,2,5-thiadiazol-3-yl)thiomethyl-3-cephem-4-carboxylic acid (syn isomer)

IR (Nujol): 3200, 1775, 1680, 1520 cm$^{-1}$

NMR (DMSO-d$_6$, δ): 3.67 (2H, broad s), 4.23, 4.60 (2H, ABq, J=14 Hz), 5.17 (1H, d, J=5 Hz), 5.73 (1H, dd, J=5 Hz, 8 Hz), 7.0 (1H, s), 7.15 (1H, t, J=72 Hz), 7.20-7.50 (15H, m), 8.73 (1H, s), 8.93 (1H, broad s), 9.83 (1H, d, J=8 Hz)

(26) 7-[2-(2-Aminothiazol-4-yl)-2-difluoromethoxyiminoacetamido]-3-(1,2,5-thiadiazol-3-yl)thiomethyl-3-cephem-4-carboxylic acid (syn isomer)

mp: 120° to 125° C. (dec.)

IR (Nujol): 3300, 3180, 1770, 1670, 1620, 1530 cm$^{-1}$

EXAMPLE 5

Water (2.7 ml) was added to a stirred solution of 7-[2-(2-tritylaminothiazol-4-yl)-2-difluoromethoxyiminoacetamido]-3-(1,3,4-thiadiazol-2-yl)thiomethyl-3-cephem-4-carboxylic acid (syn isomer) (0.9 g) in formic acid (9 ml) at 7° C. under ice-cooling and the mixture was stirred at the same temperature for 4 hours. The reaction mixture was poured into a mixture of water (150 ml) and ethyl acetate (50 ml) and adjusted to pH 2.5 with an aqueous solution of sodium bicarbonate. The separated organic layer was washed with water, dried over magnesium sulfate and evaporated in vacuo to give 7-[2-(2-aminothiazol-4-yl)-2-difluoromethoxyiminoacetamido]-3-(1,3,4-thiadiazol-2-yl)thiomethyl-3-cephem-4-carboxylic acid (syn isomer) (0.4 g).

IR (Nujol): 3300, 1770, 1670, 1530 cm$^{-1}$

NMR (DMSO-d$_6$, δ) 3.50, 3.82 (2H, ABq, J=18 Hz), 4.15, 4.57 (2H, ABq, J=14 Hz), 5.15 (1H, d, J=5 Hz), 5.76 (1H, dd, J=5 Hz, 8 Hz), 6.96 (1H, s), 7.07 (1H, t, J=72 Hz), 7.27 (2H, broad s), 9.51 (1H, s), 9.87 (1H, d, J=8 Hz)

EXAMPLE 6

The following compounds were obtained according to a similar manner to that of Example 5.

(1) 7-[2-(2-Aminothiazol-4-yl)-2-difluoromethoxyiminoacetamido]-3-(4-methyl-5-oxo-6-hydroxy-4,5-dihydro-1,2,4-triazin-3-yl)thiomethyl-3-cephem-4-carboxylic acid (syn isomer)

IR (Nujol): 1770, 1690, 1680, 1580, 1520 cm$^{-1}$ (2) 7-[2-(2-Aminothiazol-4-yl)-2-difluoromethoxyiminoacetamido]-3-(1,2,3-thiadiazol-5-yl)thiomethyl-3-cephem-4-carboxylic acid (syn isomer)

IR (Nujol): 3250, 1770, 1670, 1620, 1530 cm$^{-1}$

NMR (DMSO-d$_6$, δ): 3.52, 3.77 (2H, ABq, J=18 Hz), 4.24 (2H, broad s), 5.20 (1H, d, J=5 Hz), 5.77 (1H, dd, J=5 Hz, 8 Hz), 6.97 (1H, s), 7.10 (1H, t, J=72 Hz), 7.28 (2H, broad s), 8.85 (1H, s), 9.90 (1H, d, J=8 Hz)

(3) 7-[2-(2-Aminothiazol-4-yl)-2-difluoromethoxyiminoacetamido]-3-(3-methyl-1-pyridiniomethyl)-3-cephem-4-carboxylate (syn isomer)

IR (Nujol): 3300, 3150, 1770, 1670, 1610, 1530 cm$^{-1}$

NMR (D$_2$O, δ): 2.53 (3H, s), 3.15, 3.63 (2H, ABq, J=18 Hz), 5.27 (1H, d, J=5 Hz), 5.30, 5.52 (2H, ABq, J=14 Hz), 5.85 (1H, d, J=5 Hz), 6.87 (1H, t, J=72 Hz), 7.16 (1H, s), 7.90 (1H, dd, J=6 Hz, 8 Hz), 8.35 (1H, d, J=6 Hz), 8.72 (1H, d, J=6 Hz), 8.75 (1H, broad s)

(4) 7-[2-(2-Aminothiazol-4-yl)-2-difluoromethoxyiminoacetamido]-3-[1-(2-hydroxyethyl)-1H-tetrazol-5-yl]thiomethyl-3-cephem-4-carboxylic acid (syn isomer)

IR (Nujol): 3300, 1770, 1670, 1620, 1530 cm$^{-1}$

NMR (DMSO-d$_6$, δ): 3.20–4.10 (2H, m), 3.55, 3.88 (2H, ABq, J=18 Hz), 4.10–4.67 (2H, m), 5.15 (1H, dd, J=5 Hz), 5.78 (1H, dd, J=5 Hz, 8 Hz), 7.0 (1H, s), 7.10 (1H, t, J=72 Hz), 9.92 (1H, d, J=8 Hz)

7-[2-(2-Aminothiazol-4-yl)-2-difluoromethoxyiminoacetamido]-3-(1,2,4-thiadiazol-5-yl)thiomethyl-3-cephem-4-carboxylic acid (syn isomer)

IR (Nujol): 3250, 1770, 1670, 1620, 1530 cm$^{-1}$

NMR (DMSO-d$_6$, δ): 3.53, 3.80 (2H, ABq, J=18 Hz), 4.28, 4.62 (2H, ABq, J=14 Hz), 5.15 (1H, d, J=5 Hz), 5.78 (1H, dd, J=5 Hz, 8 Hz), 6.97 (1H, s), 7.07 (1H, t, J=72 Hz), 7.28 (2H, broad s), 8.68 (1H, s), 9.87 (1H, d, J=8 Hz)

(6) 7-[2-(2-Aminothiazol-4-yl)-2-difluoromethoxyiminoacetamido]-3-[1-{2-(N,N-dimethylamino)ethyl}-1H-tetrazol-5-yl]thiomethyl-3-cephem-4-carboxylic acid (syn isomer)

IR (Nujol): 3300, 1670, 1610, 1530 cm$^{-1}$

NMR (D$_2$O-NaHCO$_3$, δ): 2.70 (6H, s), 3.43 (2H, t, J=6 Hz), 3.45, 3.72 (2H, ABq, J=18 Hz), 4.08, 4.27 (2H, ABq, J=14 Hz), 4.68 (2H, t, J=6 Hz), 5.19 (1H, d, J=5 Hz), 5.76 (1H, dd, J=5 Hz, 8 Hz), 6.90 (1H, t, J=72 Hz), 7.23 (1H, s)

(7) 7-[2-(2-Aminothiazol-4-yl)-2-difluoromethoxyiminoacetamido]-3-[(Z)-2-cyanovinylthiomethyl]-3-cephem-4-carboxylic acid (syn isomer)

mp: 145° to 150° C. (dec.)

IR (Nujol): 3260, 2210, 1770, 1675, 1620, 1560, 1530 cm$^{-1}$ (8) 7-[2-(2-Aminothiazol-4-yl)-2-difluoromethoxyiminoacetamido]-3-(2-methyl-5-oxo-6-hydroxy-2,5-dihydro-1,2,4-triazin-3-yl)thiomethyl-3-cephem-4-carboxylic acid (syn isomer)

mp: 165° to 170° C. (dec.)

IR (Nujol): 3300, 3200, 1780, 1680, 1640, 1530 cm$^{-1}$

NMR (DMSO-d$_6$, δ): 3.60 (3H, s), 3.65 (2H, broad s), 4.10, 4.38 (2H, ABq, J=14 Hz), 5.16 (1H, d, J=5 Hz), 5.80 (1H, dd, J=5 Hz, 8 Hz), 6.97 (1H, s), 7.08 (1H, t, J=72 Hz), 7.29 (2H, broad s), 9.89 (1H, d, J=8 Hz)

(9) 7-[2-(2-Aminothiazol-4-yl)-2-difluoromethoxyiminoacetamido]-3-carbamoyloxymethyl-3-cephem-4-carboxylic acid (syn isomer)

mp: 125° to 130° C. (dec.)

IR (Nujol): 3450, 3350, 3260, 3200, 1770, 1720, 1680, 1650, 1600, 1530 cm$^{-1}$ NMR (DMSO-d$_6$, δ): 3.53 (2H, broad s), 4.63, 4.86 (2H, ABq, J=14 Hz), 5.18 (1H, d, J=5 Hz), 5.79 (1H, dd, J=5 Hz, 8 Hz), 6.56 (2H, broad s), 7.0 (1H, s), 7.10 (1H, t, J=72 Hz), 7.30 (2H, broad s), 9.86 (1H, d, J=8 Hz)

(10) 7-[2-(2-Aminothiazol-4-yl)-2-difluoromethoxyiminoacetamido]-3-(tetrazolo[1,5-b]pyridazin-6-yl)thiomethyl-3-cephem-4-carboxylic acid (syn isomer)

mp: 170° to 175° C. (dec.)

IR (Nujol): 3400, 3260, 3200, 1770, 1680, 1660, 1620, 1535 cm$^{-1}$

NMR (DMSO-d$_6$, δ): 3.63, 3.76 (2H, ABq, J=18 Hz), 4.20, 4.58 (2H, ABq, J=14 Hz), 5.15 (1H, d, J=5 Hz), 5.78 (1H, dd, J=5 Hz, 8 Hz), 6.96 (1H, s), 7.06 (1H, t, J=72 Hz), 7.29 (2H, broad s) 7.73 (1H, d, J=9 Hz), 8.55 (1H, d, J=9 Hz), 9.88 (1H, d, J=8 Hz)

(11) 7-[2-(2-Aminothiazol-4-yl)-2-difluoromethoxyiminoacetamido]-3-(1-methyl-1H-tetrazol-5-yl)thiomethyl-3-cephem-4-carboxylic acid (syn isomer)

mp: 145° to 150° C. (dec.)

IR (Nujol): 3300, 1770, 1670, 1620, 1530 cm$^{-1}$

NMR (DMSO-d$_6$, δ): 3.60, 3.73 (2H, ABq, J=18 Hz), 3.90 (3H, s), 4.20, 4.35 (2H, ABq, J=14 Hz), 5.13 (1H, d, J=5 Hz), 5.76 (1H, dd, J=5 Hz, 8 Hz), 6.96 (1H, s), 7.06 (1H, t, J=72 Hz), 7.26 (2H, broad s), 9.88 (1H, d, J=8 Hz)

(12) 7-[2-(2-Aminothiazol-4-yl)-2-difluoromethoxyiminoacetamido]-3-vinyl-3-cephem-4-carboxylic acid (syn isomer)

mp: 190° to 195° C. (dec.)

IR (Nujol): 3420, 3320, 3250, 1770, 1670, 1615, 1530 cm$^{-1}$

NMR (DMSO-d$_6$, δ): 3.56, 3.81 (2H, ABq, J=18 Hz), 5.20 (1H, d, J=5 Hz), 5.30 (1H, d, J=11 Hz), 5.58 (1H, d, J=17 Hz), 5.75 (1H, dd, J=5 Hz, 8 Hz), 6.98 (1H, s), 7.0 (1H, dd, J=11 Hz, 17 Hz), 7.08 (1H, t, J=72 Hz), 7.30 (2H, broad s), 9.90 (1H, d, J=8 Hz)

(13) 7-[2-(2-Aminothiazol-4-yl)-2-difluoromethoxyiminoacetamido]-3-(1,2,5-thiadiazol-3-yl)thiomethyl-3-cephem-4-carboxylic acid (syn isomer)

mp: 120° to 125° C. (dec.)

IR (Nujol): 3300, 3180, 1770, 1670, 1620, 1530 cm$^{-1}$

NMR (DMSO-d$_6$, δ): 3.53, 3.75 (2H, ABq, J=18 Hz), 4.18, 4.55 (2H, ABq, J=14 Hz), 5.14 (1H, d, J=5 Hz), 5.75 (1H, dd, J=5 Hz, 8 Hz), 6.96 (1H, s), 7.08 (1H, t, J=72 Hz), 7.30 (2H, broad s), 8.73 (1H, s), 9.86 (1H, d, J=8 Hz)

EXAMPLE 7

To a mixture of benzhydryl 7-[2-(2-tritylaminothiazol-4-yl)-2-difluoromethoxyiminoacetamido]-3-(4-methyl-5-oxo-6-hydroxy-4,5-dihydro-1,2,4-triazin-3-yl)thiomethyl-3-cephem-4-carboxylate (syn isomer) (1.20 g) and anisole (2.5 ml) in methylene chloride (2.5 ml) was added trifluoroacetic acid (5 ml) under ice-cooling. After being stirred for 30 minutes, the mixture was poured into diisopropyl ether (50 ml). The resultant mixture was adjusted to pH 7 with an aqueous solution of sodium bicarbonate. The separated aqueous layer was washed with ethyl acetate, acidified with 6N hydrochloric acid and extracted with a mixture of tetrahydrofuran and ethyl acetate. The extract was washed with a saturated aqueous solution of sodium chloride, dried and evaporated under reduced pressure. The residue was triturated in diethyl ether and collected by filtration to give 7-[2-(2-aminothiazol-4-yl)-2-difluoromethoxyiminoacetamido]-3-(4-methyl-5-oxo-6-hydroxy-4,5-dihydro-1,2,4-triazin-3-yl)thiomethyl-3-cephem-4-carboxylic acid (syn isomer) (600 mg).

mp: 195° to 200° C. (dec.)

IR (Nujol): 1770, 1690, 1680, 1580, 1520 cm$^{-1}$

NMR (DMSO-d$_6$, δ): 3.29 (3H, s), 3.53, 3.77 (2H, ABq, J=18 Hz), 3.99, 4.19 (2H, ABq, J=13 Hz), 5.15 (1H, d, J=5 Hz), 5.78 (1H, dd, J=5 Hz, 8 Hz), 6.98 (1H, s), 7.09 (1H, t, J=72 Hz), 7.31 (2H, s), 9.90 (1H, d, J=8 Hz), 12.41 (1H, s)

EXAMPLE 8

The following compounds were obtained according to a similar manner to that of Example 7.

(1) 7-[2-(2-Aminothiazol-4-yl)-2-difluoromethoxyiminoacetamido]-3-(1,3,4-thiadiazol-2-yl)thiomethyl-3-cephem-4-carboxylic acid (syn isomer)

IR (Nujol): 3300, 1770, 1670, 1530 cm$^{-1}$ (2) 7-[2-(2-Aminothiazol-4-yl)-2-difluoromethoxyiminoacetamido]-3-(1,2,3-thiadiazol-5-yl)thiomethyl-3-cephem-4-carboxylic acid (syn isomer)

IR (Nujol): 3250, 1770, 1670, 1620, 1530 cm$^{-1}$ (3) 7-[2-(2-Aminothiazol-4-yl)-2-difluoromethoxyiminoacetamido]-3-(3-methyl-1-pyridiniomethyl)-3-cephem-4-carboxylate (syn isomer)

IR (Nujol): 3300, 3150, 1770, 1670, 1610, 1530 cm$^{-1}$ (4) 7-[2-(2-Aminothiazol-4-yl)-2-difluoromethoxyiminoacetamido]-3-[1-(2-hydroxyethyl)-1H-tetrazol-5-yl]thiomethyl-3-cephem-4-carboxylic acid (syn isomer)

IR (Nujol): 3300, 1770, 1670, 1620, 1530 cm$^{-1}$ (5) 7-[2-(2-Aminothiazol-4-yl)-2-difluoromethoxyiminoacetamido]-3-(1,2,4-thiadiazol-5-yl)thiomethyl-3-cephem-4-carboxylic acid (syn isomer)

IR (Nujol): 3250, 1770, 1670, 1620, 1530 cm$^{-1}$ (6) 7-[2-(2-Aminothiazol-4-yl)-2-difluoromethoxyiminoacetamido]-3-[1-{2-(N,N-dimethylamino)ethyl}-1H-tetrazol-5-yl]thiomethyl-3-cephem-4-carboxylic acid (syn isomer)

IR (Nujol): 3300, 1670, 1610, 1530 cm$^{-1}$ (7) 7-[2-(2-Aminothiazol-4-yl)-2-difluoromethoxyiminoacetamido]-3-[(Z)-2-cyanovinylthiomethyl]-3-cephem-4-carboxylic acid (syn isomer)

mp: 145° to 150° C. (dec.)

IR (Nujol): 3260, 2210, 1770, 1675, 1620, 1560, 1530 cm$^{-1}$

NMR (DMSO-d$_6$, δ): 3.53, 3.63 (2H, ABq, J=18 Hz), 3.82, 4.18 (2H, ABq, J=14 Hz), 5.20 (1H, d, J=5 Hz), 5.70 (1H, d, J=11 Hz), 5.78 (1H, dd, J=5 Hz, 8 Hz), 6.98 (1H, s), 7.08 (1H, t, J=72 Hz), 7.29 (2H, broad s), 7.73 (1H, d, J=11 Hz), 9.88 (1H, d, J=8 Hz)

(8) 7-[2-(2-Aminothiazol-4-yl)-2-difluoromethoxyiminoacetamido]-3-(2-methyl-5-oxo-6-hydroxy-2,5-dihydro-1,2,4-triazin-3-yl)thiomethyl-3-cephem-4-carboxylic acid (syn isomer)

mp: 165° to 170° C. (dec.)

IR (Nujol): 3300, 3200, 1780, 1680, 1640, 1530 cm$^{-1}$ (9) 7-[2-(2-Aminothiazol-4-yl)-2-difluoromethoxyiminoacetamido]-3-carbamoyloxymethyl-3-cephem-4-cartoxylic acid (syn isomer)

mp: 125° to 130° C. (dec.)

IR (Nujol): 3450, 3350, 3260, 3200, 1770, 1720, 1680, 1650, 1600, 1530 cm$^{-1}$

(10) 7-[2-(2-Aminothiazol-4-yl)-2-difluoromethoxyiminoacetamido] acetamido]-3-(tetrazolo[1,5-b]pyridazin-6-yl)thiomethyl-3-cephem-4-carboxylic acid (syn isomer)

mp: 170° to 175° C. (dec.)

IR (Nujol): 3400, 3260, 3200, 1770, 1680, 1660, 1620, 1535 cm$^{-1}$

(11) 7-[2-(2-Aminothiazol-4-yl)-2-difluoromethoxyiminoacetamido]-3-(1-methyl-1H-tetrazol-5-yl)thiomethyl-3-cephem-4-carboxylic acid (syn isomer)

mp: 145° to 150° C. (dec.)

IR (Nujol): 3300, 1770, 1670, 1620, 1530 cm$^{-1}$

(12) 7-[2-(2-Aminothiazol-4-yl)-2-difluoromethoxyiminoacetamido]-3-vinyl-3-cephem-4-carboxylic acid (syn isomer)

mp: 190° to 195° C. (dec.)

IR (Nujol): 3420, 3320, 3250, 1770, 1670, 1615, 1530 cm$^{-1}$

(13) 7-[2-(2-Aminothiazol-4-yl)-2-difluoromethoxyiminoacetamido]-3-(1,2,5-thiadiazol-3-yl)thiomethyl-3-cephem-4-carboxylic acid (syn isomer)

mp: 120° to 125° C. (dec.)

IR (Nujol): 3300, 3180, 1770, 1670, 1620, 1530 cm$^{-1}$

EXAMPLE 9

To a mixture of benzhydryl 7-[2-(2-tritylaminothiazol-4-yl)-2-difluoromethoxyiminoacetamido]-3-chloromethyl-3-cephem-4-carboxylate (syn isomer) (1.5 g) and sodium iodide (769 mg) in N,N-dimethylformamide was added 3-mercapto-4-methyl-5-oxo-6-hydroxy-4,5-dihydro-1,2,4-triazine (816 mg). After being stirred for 45 minutes at room temperature, the reaction mixture was poured into water. The resulting precipitates were collected by filtration and dissolved in ethyl acetate. The solution was washed with water, an aqueous solution of sodium bicarbonate and a saturated aqueous solution of sodium chloride successively, dried and evaporated under reduced pressure. The residue was triturated in diisopropyl ether and collected by filtration to give benzhydryl 7-[2-(2-tritylaminothiazol-4-yl)-2-difluoromethoxyiminoacetamido]-3-(4-methyl-5-oxo-6-hydroxy-4,5-dihydro-1,2,4-triazin-3-yl)thiomethyl-3-cephem-4-carboxylate (syn isomer) (1.25 g).

IR (Nujol): 1780, 1705, 1670, 1580, 1520 cm$^{-1}$

NMR (DMSO-d$_6$, δ): 3.29 (3H, s), 3.68 (2H, m), 3.90, 4.14 (2H, ABq, J=14 Hz), 5.18 (1H, d, J=5 Hz), 5.75 (1H, dd, J=5 Hz, 8 Hz), 6.97 (1H, s), 7.03 (1H, t, J=72 Hz), 7.30 (25H, m), 9.84 (1H, d, J=8 Hz), 12.38 (1H, s)

EXAMPLE 10

To a mixture of [(Z)-2-cyanovinylthio]silver (492 mg) and acetonitrile (10 ml) was added sodium iodide (2.3 g) under stirring at 10° C.. The mixture was stirred for 15 minutes at the same temperature and cooled to 5° C., and then a solution of benzhydryl 7-[2-(2-tritylaminothiazol-4-yl)-2-difluoromethoxyiminoacetamido]-3-chloromethyl-3-cephem-4-carboxylate (syn isomer) (1.5 g) in acetonitrile (15 ml) was added thereto. The mixture was stirred for 30 minutes at 5° C. and the solvent was evaporated to give a residue. To the residue was added a mixture of ethyl acetate (50 ml) and water (30 ml). The insoluble material was filtered off and the filtrate was allowed to stand. The separated organic layer was washed with water and an aqueous solution of sodium chloride successively, and dried over magnesium sulfate. The solvent was evaporated to give a residue. The residue was triturated in diisopropyl ether and collected by filtration to give benzhydryl 7-[2-(2-tritylaminothiazol-4-yl)-2-difluoromethoxyiminoacetamido]-3-[(Z)-2-cyanovinylthiomethyl]-3-cephem-4-carboxylate (syn isomer) (1.40 g).

mp: 105° to 110° C. (dec.)

IR (Nujol): 3250, 2210, 1780, 1720, 1680, 1520, 1490 cm$^{-1}$

NMR (DMSO-d$_6$, δ): 3.63 (2H, broad s), 3.97 (2H, broad s), 5.25 (1H, d, J=5 Hz), 5.63 (1H, d, J=11 Hz), 5.78 (1H, dd, J=5 Hz, 8 Hz), 6.93 (1H, s), 7.0 (1H, s), 7.10 (1H, t, J=72 Hz), 7.15–7.60 (15H+10H+1H), 8.90 (1H, broad s), 9.87 (1H, d, J=8 Hz)

EXAMPLE 11

The following compounds were obtained according to similar manners to those of Examples 9 and 10.

(1) 7-[2-(2-Tritylaminothiazol-4-yl)-2-difluoromethoxyiminoacetamido]-3-(1,3,4-thiadiazol-2-yl)thiomethyl-3-cephem-4-carboxylic acid (syn isomer)

IR (Nujol): 3250, 1780, 1680, 1530 cm$^{-1}$ (2) 7-[2-(2-Tritylaminothiazol-4-yl)-2-difluoromethoxyiminoacetamido]-3-(1,2,3-thiadiazol-5-yl)thiomethyl-3-cephem-4-carboxylic acid (syn isomer)

IR (Nujol): 3200, 1780, 1680, 1520 cm$^{-1}$ (3) 7-[2-(2-Aminothiazol-4-yl)-2-difluoromethoxyiminoacetamido]-3-(1,3,4-thiadiazol-2-yl)thiomethyl-3-cephem-4-carboxylic acid (syn isomer)

IR (Nujol): 3300, 1770, 1670, 1530 cm$^{-1}$ (4) 7-[2-(2-Aminothiazol-4-yl)-2-difluoromethoxyiminoacetamido]-3-(4-methyl-5-oxo-6-hydroxy-4,5-dihydro-1,2,4-triazin-3-yl)thiomethyl-3-cephem-4-carboxylic acid (syn isomer)

IR (Nujol): 1770, 1690, 1680, 1580, 1520 cm$^{-1}$ (5) 7-[2-(2-Aminothiazol-4-yl)-2-difluoromethoxyiminoacetamido]-3-(1,2,3-thiadiazol-5-yl)thiomethyl-3-cephem-4-carboxylic acid (syn isomer)

IR (Nujol): 3250, 1770, 1670, 1620, 1530 cm$^{-1}$ (6) 7-[2-(2-Tritylaminothiazol-4-yl)-2-difluoromethoxyiminoacetamido]-3-[1-(2-hydroxyethyl)-1H-tetrazol-5-yl]thiomethyl-3-cephem-4-carboxylic acid (syn isomer)

IR (Nujol): 3230, 1780, 1680, 1530 cm$^{-1}$ (7) 7-[2-(2-Aminothiazol-4-yl)-2-difluoromethoxyiminoacetamido]-3-[1-(2-hydroxyethyl)-1H-tetrazol-5-yl]thiomethyl-3-cephem-4-carboxylic acid (syn isomer)

IR (Nujol): 3300, 1770, 1670, 1620, 1530 cm$^{-1}$ (8) 7-[2-(2-Tritylaminothiazol-4-yl)-2-difluoromethoxyiminoacetamido]-3-(1,2,4-thiadiazol-5-yl)thiomethyl-3-cephem-4-carboxylic acid (syn isomer)

IR (Nujol): 3300, 1780, 1650, 1590, 1530 cm$^{-1}$ (9) 7-[2-(2-Aminothiazol-4-yl)-2-difluoromethoxyiminoacetamido]-3-(1,2,4-thiadiazol-5-yl)thiomethyl-3-cephem-4-carboxylic acid (syn isomer)

IR (Nujol): 3250, 1770, 1670, 1620, 1530 cm$^{-1}$

(10) 7-[2-(2-Tritylaminothiazol-4-yl)-2-difluoromethoxyiminoacetamido]-3-[1-{2-(N,N-dimethylamino)ethyl}-1H-tetrazol-5-yl]thiomethyl-3-cephem-4-carboxylic acid (syn isomer)

IR (Nujol): 3250, 1770, 1660, 1530 cm$^{-1}$

(11) 7-[2-(2-Aminothiazol-4-yl)-2-difluoromethoxyiminoacetamido]-3-[1-{2-(N,N-dimethylamino)ethyl}-1H-tetrazol-5-yl]thiomethyl-3-cephem-4-carboxylic acid (syn isomer)

IR (Nujol): 3300, 1670, 1610, 1530 cm$^{-1}$

(12) 7-[2-(2-Tritylaminothiazol-4-yl)-2-difluoromethoxyiminoacetamido]-3-(2-methyl-5-oxo-6-hydroxy-2,5-dihydro-1,2,4-triazin-3-yl)thiomethyl-3-cephem-4-carboxylic acid (syn isomer)

mp: 125° to 130° C. (dec.)

IR (Nujol): 3200, 1780, 1655, 1590, 1530 cm$^{-1}$

(13) 7-[2-(2-Aminothiazol-4-yl)-2-difluoromethoxyiminoacetamido]-3-(2-methyl-5-oxo-6-hydroxy-2,5-dihydro-1,2,4-triazin-3-yl)thiomethyl-3-cephem-4-carboxylic acid (syn isomer)

mp: 165° to 170° C. (dec.)

IR (Nujol): 3300, 3200, 1780, 1680, 1640, 1530 cm$^{-1}$

(14) 7-[2-(2-Aminothiazol-4-yl)-2-difluoromethoxyiminoacetamido]-3-(tetrazolo[1,5-b]pyridazin-6-yl)thiomethyl-3-cephem-4-carboxylic acid (syn isomer)

mp: 170° to 175° C. (dec.)

IR (Nujol): 3400, 3260, 3200, 1770, 1680, 1660, 1620, 1535 cm$^{-1}$

(15) 7-[2-(2-Tritylaminothiazol-4-yl)-2-difluoromethoxyiminoacetamido]-3-(tetrazolo[1,5-b]pyridazin-6-yl)thiomethyl-3-cephem-4-carboxylic acid (syn isomer)

mp: 130° to 135° C. (dec.)

IR (Nujol): 3200, 1785, 1680, 1595, 1575 1530 cm$^{-1}$

(16) 7-[2-(2-Aminothiazol-4-yl)-2-difluoromethoxyiminoacetamido]-3-(1-methyl-1H-tetrazol-5-yl)thiomethyl-3-cephem-4-carboxylic acid (syn isomer)

mp: 145° to 150° C. (dec.)

IR (Nujol): 3300, 1770, 1670, 1620, 1530 cm$^{-1}$

(17) 7-[2-(2-Tritylaminothiazol-4-yl)-2-difluoromethoxyiminoacetamido]-3-(1-methyl-1H-tetrazol-5-yl)thiomethyl-3-cephem-4-carboxylic acid (syn isomer)

mp: 115° to 120° C. (dec.)

IR (Nujol): 3200, 1770, 1660, 1585, 1560, 1515 cm$^{-1}$

(18) 7-[2-(2-Tritylaminothiazol-4-yl)-2-difluoromethoxyiminoacetamido]-3-(1,2,5-thiadiazol-3-yl)thiomethyl-3-cephem-4-carboxylic acid (syn isomer)

IR (Nujol): 3200, 1775, 1680, 1520 cm$^{-1}$

(19) 7-[2-(2-Aminothiazol-4-yl)-2-difluoromethoxyiminoacetamido]-3-(1,2,5-thiadiazol-3-yl)thiomethyl-3-cephem-4-carboxylic acid (syn isomer)

mp: 120° to 125° C. (dec.)

IR (Nujol): 3300, 3180, 1770, 1670, 1620, 1530 cm$^{-1}$

(20) 7-[2-(2-Aminothiazol-4-yl)-2-difluoromethoxyiminoacetamido]-3-[(Z)-2-cyanovinylthiomethyl]-3-cephem-4-carboxylic acid (syn isomer)

mp: 145° to 150° C. (dec.)

IR (Nujol): 3260, 2210, 1770, 1675, 1620, 1560, 1530 cm$^{-1}$

(21) 7-[2-(2-Tritylaminothiazol-4-yl)-2-difluoromethoxyiminoacetamido]-3-(3-methyl-1-pyridiniomethyl)-3-cephem-4-carboxylate (syn isomer)

IR (Nujol): 3300, 1780, 1670, 1620, 1530 cm$^{-1}$

(22) 7-[2-(2-Aminothiazol-4-yl)-2-difluoromethoxyiminoacetamido]-3-(3-methyl-1-pyridiniomethyl)-3-cephem-4-carboxylate (syn isomer)

IR (Nujol): 3300, 3150, 1770, 1670, 1610, 1530 cm$^{-1}$

EXAMPLE 12

To a solution of N,N-dimethylformamide (438 mg) in ethyl acetate (5 ml) was added phosphorus oxychloride (0.92 g) at 0° C. and the mixture was stirred for 30 minutes at the same temperature to give a Vilsmeier reagent. To the Vilsmeier reagent was added a mixture of 2-(2-tritylaminothiazol-4-yl)-2-difluoromethoxyiminoacetic acid (syn isomer) (2.39 g) and ethyl acetate (15 ml) at 0° C. and the mixture was stirred for 30 minutes at the same temperature to give an activated acid solution. On the other hand, a mixture of 7-amino-3-(1-methyl-4-pyridiniothiomethyl)-3-cephem-4-carboxylate (2.36 g), N-trimethylsilylacetamide (13 g) and tetrahydrofuran (30 ml) was stirred for one hour at 30° C., cooled to −20° C. and added all at once to the above obtained activated acid solution at −20° C., and the mixture was stirred for one hour at −20° to −10° C. The reaction mixture was poured into a mixture of ethyl acetate (60 ml) and water (60 ml), the organic layer was separated and the aqueous layer was extracted with ethyl acetate. The organic layer was combined and washed with an aqueous solution of sodium chloride, dried over magnesium sulfate and evaporated. The residue was triturated with diisopropyl ether to give 7-[2-(2-tritylaminothiazol-4-yl)-2-difluoromethoxyiminoacetamido]-3-(1-methyl-4-pyridiniothiomethyl)-3-cephem-4-carboxylate (syn isomer) (2.64 g).

EXAMPLE 13

To a solution of 2-(2-aminothiazol-4-yl)-2-difluoromethoxyiminoacetic acid (syn isomer) (948 mg) in N,N-dimethylformamide (20 ml) were added diisopropylethylamine (1.04 g) and mesyl chloride (920 mg) at −50° C., and the mixture was stirred for 30 minutes at the same temperature. On the other hand, a mixture of 7-amino-3-hydroxymethyl-3-cephem-4-carboxylic acid (1.0 g), N-trimethylsilylacetamide (16 g) and tetrahydrofuran (32 ml) was stirred for one hour at room temperature, cooled to −45° C. and added all at once to the above obtained activated acid solution, and the mixture was stirred for 2 hours at −40° to −30° C. The reaction mixture was poured into a solution of sodium bicarbonate (1.68 g) in water (100 ml) and the mixture was washed with ethyl acetate (50 ml). The aqueous solution was adjusted to pH 3–4 with 10% hydrogen chloride, salted out and extracted twice with a mixture of tetrahydrofuran (50 ml) and ethyl acetate (50 ml). The extract was washed three times with an aqueous solution of sodium chloride and dried over magnesium sulfate. To the extract was added a solution of sodium 2-ethylhexanoate (0.66 g) in ether (25 ml) and the resulting precipitates were collected by filtration to give sodium 7-[2-(2-aminothiazol-4-yl)-2-difluoromethoxyiminoacetamido]-3-hydroxymethyl-3-cephem-4-carboxylate (syn isomer) (0.73 g).

IR (Nujol): 3300, 1750, 1665, 1600, 1525 cm$^{-1}$

NMR (D$_2$O, δ): 3.50, 3.60 (2H, ABq, J=18 Hz), 4.27 (2H, s), 5.20 (1H, d, J=5 Hz), 5.78 (1H, d, J=5 Hz), 6.90 (1H, t, J=71 Hz), 7.22 (1H, s)

EXAMPLE 14

The following compounds were obtained according to similar manners to those of Example 1 to 3, 12 and 13.

(1) Benzhydryl 7-[2-(2-tritylaminothiazol-4-yl)-2-difluoromethoxyiminoacetamido]-3-(3-methyl-1,2,4-thiadiazol-5-yl)thiomethyl-3-cephem-4-carboxylate (syn isomer)

IR (Nujol): 3250, 1790, 1725, 1690, 1600, 1530 cm$^{-1}$ (2) 7-[2-(2-Aminothiazol-4-yl)-2-difluoromethoxyiminoacetamido]-3-(3-methyl-1,2,4-thiadiazol-5-yl)thiomethyl-3-cephem-4-carboxylic acid (syn isomer)
mp: 135°–140° C. (dec.)

IR (Nujol): 3300, 3200, 1775, 1670, 1620, 1530 cm$^{-1}$ (3) 7-[2-(2-Tritylaminothiazol-4-yl)-2-difluoromethoxyiminoacetamido]-3-(4-carboxy-3-hydroxy-1,2-thiazol-5-yl)thiomethyl-3-cephem-4-carboxylic acid (syn isomer)

IR (Nujol): 3200, 1780, 1710, 1670, 1650, 1590, 1525 cm$^{-1}$ (4) 7-[2-(2-Aminothiazol-4-yl)-2-difluoromethoxyiminoacetamido]-3-(4-carboxy-3-hydroxy-1,2-thiazol-5-yl)thiomethyl-3-cephem-4-carboxylic acid (syn isomer)
mp: 180°–185° C. (dec.)

IR (Nujol): 3300, 1760, 1660, 1600, 1530 cm$^{-1}$ (5) 7-[2-(2-Tritylaminothiazol-4-yl)-2-difluoromethoxyiminoacetamido]-3-(5-methyl-1,3,4-thiadiazol-2-yl)thiomethyl-3-cephem-4-carboxylic acid (syn isomer)

IR (Nujol): 3200, 1780, 1680, 1530 cm$^{-1}$

NMR (DMSO-d$_6$, δ): 2.67 (3H, s), 3.60 (2H, m), 4.17, 4.58 (2H, ABq, J=14 Hz), 5.15 (1H, d, J=5 Hz), 5.70 (1H, dd, J=5 Hz, 8 Hz), 6.98 (1H, s), 7.07 (1H, t, J=72 Hz), 7.10–7.67 (15H, m), 8.92 (1H, broad s), 9.85 (1H, d, J=8 Hz)

(6) 7-[2-(2-Aminothiazol-4-yl)-2-difluoromethoxyiminoacetamido]-3-(5-methyl-1,3,4-thiadiazol-2-yl)thiomethyl-3-cephem-4-carboxylic acid (syn isomer)

IR (Nujol): 3250, 1770, 1680, 1610, 1530 cm$^{-1}$ (7) 7-[2-(2-Tritylaminothiazol-4-yl)-2-difluoromethoxyiminoacetamido]-3-cephem-4-carboxylic acid (syn isomer)

IR (Nujol): 3200, 1780, 1720 (s), 1680, 1630, 1590, 1530 cm$^{-1}$

NMR (DMSO-d$_6$, δ): 3.60 (2H, m), 5.12 (1H, d, J=5 Hz), 5.83 (1H, dd, J=5 Hz, 8 Hz), 7.00 (1H, s), 7.10 (1H, t, J=72 Hz), 8.92 (1H, broad s), 9.87 (1H, d, J=8 Hz)

(8) 7-[2-(2-Aminothiazol-4-yl)-2-difluoromethoxyiminoacetamido]-3-cephem-4-carboxylic acid (syn isomer)

NMR (DMSO-d$_6$, δ): 3.62 (2H, m), 5.12 (1H, d, J=5 Hz), 5.85 (1H, dd, J=5 Hz, 8 Hz), 6.47 (1H, t, J=2 Hz), 6.98 (1H, s), 7.09 (1H, t, J=72 Hz), 7.30 (2H, broad s), 9.90 (1H, d, J=8 Hz)

(9) 7-[2-(2-Tritylaminothiazol-4-yl)-2-difluoromethoxyiminoacetamido]-3-(3-ethyl-1-pyridiniomethyl)-3-cephem-4-carboxylate (syn isomer)

IR (Nujol): 1780, 1680, 1630, 1590, 1530 cm$^{-1}$

NMR (DMSO-d$_6$, δ): 1.17 (3H, t, J=7 Hz), 3.55 (2H, ABq, J=7 Hz), 3.25–3.72 (2H, m), 5.20 (1H, d, J=5 Hz), 5.42, 5.58 (2H, ABq, J=14 Hz), 5.67 (1H, dd, J=5 Hz, 8 Hz), 6.95 (1H, s), 7.05 (1H, t, J=72 Hz), 7.00–7.67 (15H, m), 8.53 (1H, d, J=8 Hz), 8.93 (1H, broad s), 8.83–9.17 (2H, m), 9.85 (1H, d, J=8 Hz)

(10) 7-[2-(2-Aminothiazol-4-yl)-2-difluoromethoxyiminoacetamido]-3-(3-ethyl-1-pyridiniomethyl)-3-cephem-4-carboxylate (syn isomer)

IR (Nujol): 3270, 1770, 1670, 1610, 1530 cm$^{-1}$

(11) 7-[2-(2-Aminothiazol-4-yl)-2-difluoromethoxyiminoacetamido]-3-(4-methoxy-1-pyridiniomethyl)-3-cephem-4-carboxylate (syn isomer)

IR (Nujol): 3300, 3150, 1770, 1670, 1635, 1610, 1560, 1515 cm$^{-1}$

(12) 7-[2-(2-Aminothiazol-4-yl)-2-difluoromethoxyiminoacetamido]-3-(3-mesyl-1-pyridiniomethyl)-3-cephem-4-carboxylate (syn isomer)

IR (Nujol): 3300, 3160, 1770, 1670, 1610, 1530 cm$^{-1}$

(13) 7-[2-(2-Aminothiazol-4-yl)-2-difluoromethoxyiminoacetamido]-3-(4-mesyl-1-pyridiniomethyl)-3-cephem-4-carboxylate (syn isomer)

NMR (DMSO-d$_6$, δ): 3.23, 3.66 (2H, ABq, J=18 Hz), 3.45 (3H, s), 5.26 (1H, d, J=5 Hz), 5.45, 5.70 (2H, ABq, J=14 Hz), 5.80 (1H, d, J=5 Hz), 6.88 (1H, t, J=71 Hz), 7.16 (1H, s), 8.58 (2H, d, J=6 Hz), 9.35 (2H, d, J=6 Hz)

(14) 7-[2-(2-Aminothiazol-4-yl)-2-difluoromethoxyiminoacetamido]-3-(3-methylthio-1-pyridiniomethyl)-3-cephem-4-carboxylate (syn isomer)

IR (Nujol): 3300, 3200, 1770, 1660, 1610, 1530 cm$^{-1}$

(15) 7-[2-(2-Aminothiazol-4-yl)-2-difluoromethoxyiminoacetamido]-3-(1-methyl-4-pyridiniothiomethyl)-3-cephem-4-carboxylate (syn isomer)

IR (Nujol): 3300, 1765, 1670, 1630, 1600, 1535 cm$^{-1}$

(16) Benzhydryl 7-[2-(2-tritylaminothiazol-4-yl)-2-difluoromethoxyiminoacetamido]-3-[(E)-2-(3-pyridylthio)vinyl]-3-cephem-4-carboxylate (syn isomer)

NMR (DMSO-d$_6$, δ): 3.67–4.0 (2H, m), 5.25 (1H, d, J=5 Hz), 5.77 (1H, dd, J=5 Hz, 8 Hz), 6.53 (1H, d, J=16 Hz), 6.90–7.70 (4H+25H), 7.70–9.0 (4H, m), 9.90 (1H, d, J=8 Hz)

(17) Benzhydryl 7-[2-(2-tritylaminothiazol-4-yl)-2-difluoromethoxyiminoacetamido]-3-[(E)-2-(1-methyl-3- pyridiniothio)vinyl]-3-cephem-4-carboxylate iodide (syn isomer)

NMR (DMSO-d$_6$, δ): 3.70, 4.0 (2H, ABq, J=18 Hz), 4.30 (3H, s), 5.27 (1H, d, J=5 Hz), 5.80 (1H, dd, J=5 Hz, 8 Hz), 6.47 (1H, d, J=16 Hz), 6.90–7.60 (4H+25H), 7.90–9.10 (4H, m), 9.92 (1H, d, J=8 Hz)

(18) 7-[2-(2-Aminothiazol-4-yl)-2-difluoromethoxyiminoacetamido]-3-[(E)-2-(1-methyl-3-pyridiniothio)-vinyl]-3-cephem-4-carboxylate (syn isomer)

IR (Nujol): 3300, 3170, 1760, 1665, 1600, 1530, 1490 cm$^{-1}$

(19) Benzhydryl 7-[2-(2-tritylaminothiazol-4-yl)-2-difluoromethoxyiminoacetamido]-3-(1-methyl-3-pyridiniothiomethyl)-3-cephem-4-carboxylate iodide (syn isomer)

NMR (DMSO-d$_6$, δ): 3.40–3.90 (2H, m), 3.90–4.40 (2H, m), 4.20 (3H, s), 5.25 (1H, d, J=5 Hz), 5.90 (1H, dd, J=5 Hz, 8 Hz), 6.70–7.60 (3H+25H), 7.70–8.0 (1H, m), 8.20–8.50 (1H, m), 8.60–8.83 (1H, m), 8.97 (1H, s), 9.83 (1H, d, J=8 Hz)

(20) 7-[2-(2-Aminothiazol-4-yl)-2-difluoromethoxyiminoacetamido]-3-(1-methyl-3-pyridiniothiomethyl)-3cephem-4-carboxylate (syn isomer)

IR (Nujol): 3300, 3180, 1760, 1670, 1600, 1530 cm$^{-1}$

(21) Benzhydryl 7-[2-(2-tritylaminothiazol-4-yl)-2-difluoromethoxyiminoacetamido]-3-chloromethyl-3-cephem-4-carboxylate-1-oxide (syn isomer)

NMR (DMSO-d$_6$, δ): 3.30, 3.73 (2H, ABq, J=18 Hz), 4.45 (2H, broad s), 5.27 (1H, d, J=5 Hz), 5.78 (1H, dd, J=5 Hz, 8 Hz), 6.90–7.60 (3H+25H), 8.90 (1H, broad s), 9.88 (1H, d, J=8 Hz)

(22) Benzhydryl 7-[2-(2-tritylaminothiazol-4-yl)-2-difluoromethoxyiminoacetamido]-3-iodomethyl-3cephem-4-carboxylate-1-oxide (syn isomer)

NMR (DMSO-d$_6$, δ): 3.0–4.0 (2H, m), 4.40 (2H, broad s), 5.05 (1H, d, J=5 Hz), 5.80 (1H, d, J=5 Hz, 8 Hz), 6.70–7.80 (3H+25H), 8.85 (1H, broad s), 9.53 (1H, d, J=8 Hz)

(23) Benzhydryl 7-[2-(2-tritylaminothiazol-4-yl)-2-difluoromethoxyiminoacetamido]-3-(1-methyl-1-pyrrolidiniomethyl)-3-cephem-4-carboxylate-1-oxide iodide (syn isomer)

NMR (DMSO-d$_6$, δ): 1.73–2.20 (4H, m), 2.80 (3H, s), 3.10–3.50 (4H, m), 3.90–4.60 (2H), 5.13 (1H, d, J=5 Hz), 5.90 (1H, dd, J=5 Hz, 8 Hz), 7.0–7.70 (10H+15H+2H), 8.83 (1H, s), 9.67 (1H, d, J=8 Hz)

(24) Benzhydryl 7-[2-(2-tritylaminothiazol-4-yl)-2-difluoromethoxyiminoacetamido]-3-(1-methyl-1-pyrrolidiniomethyl)-3-cephem-4-carboxylate trifluoroacetate (syn isomer)

NMR (DMSO-d$_6$, δ): 1.70–2.20 (4H), 2.70 (3H, s), 3.0–4.0 (2H+4H), 4.10, 4.50 (2H), 5.33 (1H, d, J=5 Hz), 5.87 (1H, dd, J=5 Hz, 8 Hz), 7.0–7.70 (10H+15H+2H), 8.93 (1H, s), 9.90 (1H, d, J=8 Hz)

(25) 7-[2-(2-Aminothiazol-4-yl)-2-difluoromethoxyiminoacetamido]-3-(1-methyl-1-pyrrolidiniomethyl)-3-cephem-4-carboxylate (syn isomer)

IR (Nujol): 3300, 3180, 1770, 1670, 1610, 1535 cm$^{-1}$

EXAMPLE 15

A mixture of 7-[2-(2-tritylaminothiazol-4-yl)-2-difluoromethoxyiminoacetamido]-3-(1-methyl-4-pyridiniothiomethyl)-3-cephem-4-carboxylate (syn isomer) (2.58 g), formic acid (25 ml) and water (7.5 ml) was stirred for 3.0 hours at 0° C. and evaporated. The residue was triturated with acetone and dissolved in water (200 ml). The mixture was adjusted to pH 3.0 with an aqueous solution of sodium bicarbonate and the precipitates were filtered off. The aqueous layer was subjected to column chromatography on macroporus non-ionic adsorption resin "Diaion HP-20", and the elution was carried out with 30% aqueous solution of methanol. The fractions containing the object compound were collected, concentrated in vacuo and lyophilized to give 7-[2-(2-aminothiazol-4-yl)-2-difluoromethoxyiminoacetamido]-3-(1-methyl-4-pyridiniothiomethyl)-3-cephem-4-carboxylate (syn isomer) (270 mg).

IR (Nujol): 3300, 1765, 1670, 1630, 1600, 1535 cm$^{-1}$

NMR (D$_2$O+DMSO-d$_6$, δ): 3.43, 3.70 (2H, ABq, J=15 Hz), 4.16 (3H, s), 4.16, 4.42 (2H, ABq, J=14 Hz), 5.13 (1H, d, J=5 Hz), 5.73 (1H, d, J=5 Hz), 6.91 (1H, t, J=71 Hz), 7.16 (1H, s), 7.78 (2H, d, J=7 Hz), 8.35 (2H, d, J=7 Hz)

EXAMPLE 16

The following compounds were obtained according to similar manners to those of Examples 5 and 15.

(1) 7-[2-(2-Aminothiazol-4-yl)-2-difluoromethoxyiminoacetamido]-3-(3-methyl-1,2,4-thiadiazol-5-yl)thiomethyl-3-cephem-4-carboxylic acid (syn isomer)

mp: 135°–140° C. (dec.)

IR (Nujol): 3300, 3200, 1775, 1670, 1620, 1530 cm$^{-1}$ (2) 7-[2-(2-Aminothiazol-4-yl)-2-difluoromethoxyiminoacetamido]-3-(4-carboxy-3-hydroxy-1,2-thiazol-5-yl)thiomethyl-3-cephem-4-carboxylic acid (syn isomer)

mp: 180°–185° C. (dec.)

IR (Nujol): 3300, 1760, 1660, 1600, 1530 cm$^{-1}$

NMR (DMSO-d$_6$, δ): 3.67 (2H, broad s), 4.20 (2H, broad s), 5.22 (1H, d, J=5 Hz), 5.80 (1H, dd, J=5 Hz, 8 Hz), 7.0 (1H, s), 7.10 (1H, t, J=72 Hz), 9.90 (1H, d, J=8 Hz)

(3) 7-[2-(2-Aminothiazol-4-yl)-2-difluoromethoxyiminoacetamido]-3-(5-methyl-1,3,4-thiadiazol-2-yl)thiomethyl-3-cephem-4-carboxylic acid (syn isomer)

IR (Nujol): 3250, 1770, 1680, 1610, 1530 cm$^{-1}$

NMR (DMSO-d$_6$, δ): 2.68 (3H, s), 3.55, 3.80 (2H, ABq, J=18 Hz), 4.20, 4.53 (2H, ABq, J=14 Hz), 5.17 (1H, d, J=5 Hz), 5.77 (1H, dd, J=5 Hz, 8 Hz), 6.99 (1H, s), 7.08 (1H, t, J=72 Hz), 7.23 (2H, broad s), 9.90 (1H, d, J=8 Hz)

(4) 7-[2-(2-Aminothiazol-4-yl)-2-difluoromethoxyiminoacetamido]-3-cephem-4-carboxylic acid (syn isomer)

NMR (DMSO-d$_6$, δ): 3.62 (2H, m), 5.12 (1H, d, J=5 Hz), 5.85 (1H, dd, J=5 Hz, 8 Hz), 6.47 (1H, t, J=2 Hz), 6.98 (1H, s), 7.09 (1H, t, J=72 Hz), 7.30 (2H, broad s), 9.90 (1H, d, J=8 Hz)

(5) 7-[2-(2-Aminothiazol-4-yl)-2-difluoromethoxyiminoacetamido]-3-(3-ethyl-1-pyridiniomethyl)-3-cephem-4-carboxylate (syn isomer)

IR (Nujol): 3270, 1770, 1670, 1610, 1530 cm$^{-1}$

NMR (D$_2$O+NaHCO$_3$, δ): 1.27 (3H, t, J=7 Hz), 2.87 (2H, q, J=7 Hz), 3.15, 3.63 (2H, ABq, J=18 Hz), 5.24 (1H, d, J=7 Hz), 5.27, 5.52 (2H, ABq, J=14 Hz), 5.87 (1H, d, J=5 Hz), 6.87 (1H, t, J=72 Hz), 7.15 (1H, s), 7.93 (1H, dd, J=6 Hz, 8 Hz), 8.40 (1H, d, J=8 Hz), 8.73 (1H, d, J=6 Hz), 8.77 (1H, s)

(6) 7-[2-(2-Aminothiazol-4-yl)-2-difluoromethoxyiminoacetamido]-3-(4-methoxy-1-pyridiniomethyl)-3-cephem-4-carboxylate (syn isomer)

IR (Nujol): 3300, 3150, 1770, 1670, 1635, 1610, 1560, 1515 cm$^{-1}$ (7) 7-[2-(2-Aminothiazol-4-yl)-2-difluoromethoxyiminoacetamido]-3-(3-mesyl-1-pyridiniomethyl)-3-cephem-4-carboxylate (syn isomer)

IR (Nujol): 3300, 3160, 1770, 1670, 1610, 1530 cm$^{-1}$ (8) 7-[2-(2-Aminothiazol-4-yl)-2-difluoromethoxyiminoacetamido]-3-(4-mesyl-1-pyridiniomethyl)-3-cephem-4-carboxylate (syn isomer)

NMR (DMSO-$d_6$, δ): 3.23, 3.66 (2H, ABq, J=18 Hz), 3.45 (3H, s), 5.26 (1H, d, J=5 Hz), 5.45, 5.70 (2H, ABq, J=14 Hz), 5.80 (1H, d, J=5 Hz), 6.88 (1H, t, J=71 Hz), 7.16 (1H, s), 8.58 (2H, d, J=6 Hz), 9.35 (2H, d, J=6 Hz)

(9) 7-[2-(2-Aminothiazol-4-yl)-2-difluoromethoxyiminoacetamido]-3-(3-methylthio-1-pyridiniomethyl)-3cephem-4-carboxylate (syn isomer)

IR (Nujol): 3300, 3200, 1770, 1660, 1610, 1530 cm$^{-1}$

(10) 7-[2-(2-Aminothiazol-4-yl)-2-difluoromethoxyiminoacetamido]-3-[(E)-2-(1-methyl-3-pyridiniothio)-vinyl]-3-cephem-4-carboxylate (syn isomer)

IR (Nujol): 3300, 3170, 1760, 1665, 1600, 1530, 1490 cm$^{-1}$

(11) 7-[2-(2-Aminothiazol-4-yl)-2-difluoromethoxyiminoacetamido]-3-(1-methyl-3-pyridiniothiomethyl)-3-cephem-4-carboxylate (syn isomer)

IR (Nujol): 3300, 3180, 1760, 1670, 1600, 1530 cm$^{-1}$

(12) 7-[2-(2-Aminothiazol-4-yl)-2-difluoromethoxyiminoacetamido]-3-(1-methyl-1-pyrrolidiniomethyl)-3-cephem-4-carboxylate (syn isomer)

IR (Nujol): 3300, 3180, 1770, 1670, 1610, 1535 cm$^{-1}$

(13) Sodium 7-[2-(2-aminothiazol-4-yl)-2-difluoromethoxyiminoacetamido]-3-hydroxymethyl-3-cephem-4-carboxylate (syn isomer)

IR (Nujol): 3300, 1750, 1665, 1600, 1525 cm$^{-1}$

EXAMPLE 17

A solution of benzhydryl 7-[2-(2-tritylaminothiazol-4-yl)-2-difluoromethoxyiminoacetamido]-3-(1-methyl-1-pyrrolidiniomethyl)-3-cephem-4-carboxylate trifluoroacetate (syn isomer) (1.25 g) in methylene chloride (4 ml) was stirred at 0°-5° C., and anisole (2.6 ml) and trifluoroacetic acid (5.2 ml) were added thereto. The mixture was stirred for one hour at 0°-5° C. To the reaction mixture was added diisopropyl ether, and the resultant precipitates were collected by filtration, washed with diisopropyl ether and dissolved in water (400 ml). The solution was subjected to column chromatography on macroporus non-ionic adsorption resin "Diaion HP-20" and the elution was carried out with 30% aqueous solution of methanol. The fractions containing the object compound were collected, concentrated in vacuo and lyophilized to give 7-[2-(2-aminothiazol-4-yl)-2-difluoromethoxyiminoacetamido]-3-(1-methyl-1-pyrrolidiniomethyl)-3-cephem-4-carboxylate (syn isomer) (450 mg).

IR (Nujol): 3300, 3180, 1770, 1670, 1610, 1535 cm$^{-1}$

NMR ($D_2O$, δ): 2.0-2.40 (4H), 2.96 (3H, s), 3.30-3.70 (4H), 3.43, 3.90 (2H, ABq, J=18 Hz), 3.95, 4.72 (2H, ABq, J=14 Hz), 5.33 (1H, d, J=5 Hz), 5.85 (1H, dd, J=5 Hz, 8 Hz), 6.89 (1H, t, J=7 Hz), 7.20 (1H, s)

EXAMPLE 18

A solution of benzhydryl 7-[2-(2-tritylaminothiazol-4-yl)-2-difluoromethoxyiminoacetamido]-3-[(E)-2-(1-methyl-3-pyridiniothio)vinyl]-3-cephem-4-carboxylate iodide (syn isomer) (1.9 g), tetrahydrofuran (60 ml) and water (4 ml) was subjected to column chromatography on Amberlite IRA-400 ($CF_3COO^\ominus$ form) [Trademark, prepared by Rohm & Hass Co.] and the elution was carried out with a solution of water and tetrahydrofuran (1:15). The fractions containing the compound were collected and evaporated. The residue was triturated with diisopropyl ether to give benzhydryl 7-[2-(2-tritylaminothiazol-4-yl)-2-difluoromethoxyiminoacetamido]-3-[(E)-2-(1-methyl-3-pyridiniothio)-vinyl]-3-cephem-4-carboxylate trifluoroacetate (syn isomer) (1.65 g). This compound was treated according to a similar manner to that of Example 17 to give 7-[2-(2-aminothiazol-4-yl)-2-difluoromethoxyiminoacetamido]-3-[(E)-2-(1-methyl-3-pyridiniothio)-vinyl]-3-cephem-4-carboxylate (syn isomer).

IR (Nujol): 3300, 3170, 1760, 1665, 1600, 1530, 1490 cm$^{-1}$

NMR (DMSO-$d_6$+$D_2O$, δ): 3.69 (2H, broad s), 4.30 (3H, s), 5.20 (1H, d, J=5 Hz), 5.71 (1H, d, J=5 Hz), 6.58 (1H, d, J=16 Hz), 6.94 (1H, t, J=71 Hz), 7.13 (1H, d, J=16 Hz), 7.15 (1H, s), 7.76-8.0 (1H, m), 8.26-8.46 (1H, m), 8.46-8.63 (1H, m), 8.69 (1H, s)

EXAMPLE 19

The following compounds were obtained according to similar manners to those of Examples 7 and 17.

(1) 7-[2-(2-Aminothiazol-4-yl)-2-difluoromethoxyiminoacetamido]-3-(3-methyl-1,2,4-thiadiazol-5-yl)thiomethyl-3-cephem-4-carboxylic acid (syn isomer)

mp: 135°-140° C. (dec.)

IR (Nujol): 3300, 3200, 1775, 1670, 1620, 1530 cm$^{-1}$

NMR (DMSO-$d_6$, δ): 2.53 (3H, s), 3.55, 3.76 (2H, ABq, J=18 Hz), 4.25, 4.62 (2H, ABq, J=14 Hz), 5.16 (1H, d, J=5 Hz), 5.80 (1H, dd, J=5 Hz, 8 Hz), 7.0 (1H, s), 7.10 (1H, t, J=72 Hz), 7.30 (2H, broad s), 9.88 (1H, d, J=8 Hz)

(2) 7-[2-(2-Aminothiazol-4-yl)-2-difluoromethoxyiminoacetamido]-3-(4-carboxy-3-hydroxy-1,2-thiazol-5-yl)thiomethyl-3-cephem-4-carboxylic acid (syn isomer)

mp: 180°-185° C. (dec.)

IR (Nujol): 3300, 1760, 1660, 1600, 1530 cm$^{-1}$ (3) 7-[2-(2-Aminothiazol-4-yl)-2-difluoromethoxyiminoacetamido]-3-(5-methyl-1,3,4-thiadiazol-2-yl)thiomethyl-3-cephem-4-carboxylic acid (syn isomer)

IR (Nujol): 3250, 1770, 1680, 1610, 1530 cm$^{-1}$ (4) 7-[2-(2-Aminothiazol-4-yl)-2-difluoromethoxyiminoacetamido]-3-cephem-4-carboxylic acid (syn isomer)

NMR (DMSO-$d_6$, δ): 3.62 (2H, m), 5.12 (1H, d, J=5 Hz), 5.85 (1H, dd, J=5 Hz, 8 Hz), 6.47 (1H, t, J=2 Hz), 6.98 (1H, s), 7.09 (1H, t, J=72 Hz), 7.30 (2H, broad s), 9.90 (1H, d, J=8 Hz)

(5) 7-[2-(2-Aminothiazol-4-yl)-2-difluoromethoxyiminoacetamido]-3-(3-ethyl-1-pyridiniomethyl)-3-cephem-4-carboxylate (syn isomer)

IR (Nujol): 3270, 1770, 1670, 1610, 1530 cm$^{-1}$ (6) 7-[2-(2-Aminothiazol-4-yl)-2-difluoromethoxyiminoacetamido]-3-(4-methoxy-1-pyridiniomethyl)-3-cephem-4-carboxylate (syn isomer)

IR (Nujol): 3300, 3150, 1770, 1670, 1635, 1610, 1560, 1515 cm$^{-1}$ (7) 7-[2-(2-Aminothiazol-4-yl)-2-difluoromethoxyiminoacetamido]-3-(3-mesyl-1-pyridiniomethyl)-3-cephem-4-carboxylate (syn isomer)

IR (Nujol): 3300, 3160, 1770, 1670, 1610, 1530 cm$^{-1}$ (8) 7-[2-(2-Aminothiazol-4-yl)-2-difluoromethoxyiminoacetamido]-3-(4-mesyl-1-pyridiniomethyl)-3-cephem-4-carboxylate (syn isomer)

NMR (DMSO-$d_6$, δ): 3.23, 3.66 (2H, ABq, J=18 Hz), 3.45 (3H, s), 5.26 (1H, d, J=5 Hz), 5.45, 7.50 (2H, ABq, J=14 Hz), 5.80 (1H, d, J=5 Hz), 6.88 (1H, t, J=71 Hz), 7.16 (1H, s), 8.58 (2H, d, J=6 Hz), 9.35 (2H, d, J=6 Hz)

(9) 7-[2-(2-Aminothiazol-4-yl)-2-difluoromethoxyiminoacetamido]-3-(3-methylthio-1-pyridiniomethyl)-3-cephem-4-carboxylate (syn isomer)

IR (Nujol): 3300, 3200, 1770, 1660, 1610, 1530 cm$^{-1}$

(10) 7-[2-(2-Aminothiazol-4-yl)-2-difluoromethoxyiminoacetamido]-3-(1-methyl-4-pyridiniothiomethyl)-3-cephem-4-carboxylate (syn isomer)

IR (Nujol): 3300, 1765, 1670, 1630, 1600, 1535 cm$^{-1}$

(11) 7-[2-(2-Aminothiazol-4-yl)-2-difluoromethoxyiminoacetamido]-3-(1-methyl-3-pyridiniothiomethyl)-3-cephem-4-carboxylate (syn isomer)

IR (Nujol): 3300, 3180, 1760, 1670, 1600, 1530 cm$^{-1}$

NMR (DMSO-$d_6$, δ): 2.95–3.60 (2H), 4.18, 4.40 (2H, ABq, J=14 Hz), 4.26 (3H, s), 4.96 (1H, d, J=5 Hz), 5.50 (1H, dd, J=5 Hz, 8 Hz), 6.93 (1H, s), 7.03 (1H, t, J=71 Hz), 7.28 (2H, broad s) 7.70–7.96 (1H, m), 8.36–8.73 (2H, m), 9.67 (1H, d, J=8 Hz), 9.70 (1H, s)

(12) Sodium 7-[2-(2-aminothiazol-4-yl)-2-difluoromethoxyiminoacetamido]-3-hydroxymethyl-3-cephem-4-carboxylate (syn isomer)

IR (Nujol): 3300, 1750, 1665, 1600, 1525 cm$^{-1}$

EXAMPLE 20

A mixture of 7-[2-(2-aminothiazol-4-yl)-2-difluoromethoxyiminoacetamido]-3-acetoxymethyl-3-cephem-4-carboxylic acid (syn isomer) (3.0 g), 4-methoxypyridine (4.0 g), sodium iodide (8.0 g), acetonitrile (4.0 ml) and water (1.0 ml) was heated for 2.0 hours at 65° to 68° C., and then water (100 ml) was added thereto. The mixture was adjusted to pH 3.0 with 1N-hydrogen chloride and the resultant precipitates were filtered off. The aqueous layer was subjected to column chromatography on macroporus nonionic adsorption resin "Diaion HP-20" and the elution was carried out with 30% aqueous methanol. The fractions containing the object compound were collected, concentrated in vacuo and lyophilized to give 7-[2-(2-aminothiazol-4-yl)-2-difluoromethoxyiminoacetamido]-3-(4-methoxy-1-pyridiniomethyl)-3-cephem-4-carboxylate (syn isomer) (0.43 g).

IR (Nujol): 3300, 3150, 1770, 1670, 1635, 1610, 1560, 1515 cm$^{-1}$

NMR (D$_2$O, δ): 3.62, 3.20 (2H, ABq, J=18 Hz), 4.10 (3H, s), 5.26 (1H, d, J=5 Hz), 5.35, 5.13 (2H, ABq, J=14 Hz), 5.82 (1H, d, J=5 Hz), 6.88 (1H, t, J=71 Hz), 7.13 (1H, s), 7.42 (2H, d, J=7 Hz), 8.65 (2H, d, J=7 Hz)

EXAMPLE 21

A solution of benzhydryl 7-[2-(2-tritylaminothiazol-4-yl)-2-difluoromethoxyiminoacetamido]-3-iodomethyl-3-cephem-4-carboxylate-1-oxide (syn isomer) (1.97 g) and N-methylpyrrolidine (204 mg) in tetrahydrofuran (10 ml) was stirred for 40 minutes at 0°–5° C. and then diisopropyl ether was added thereto. The resultant precipitates were collected by filtration, washed with diisopropyl ether and air-dried to give benzhydryl 7-[2-(2-tritylaminothiazol-4-yl)-2-difluoromethoxyiminoacetamido]-3-(1-methyl-1-pyrrolidiniomethyl)-3-cephem-4-carboxylate-1-oxide iodide (syn isomer) (2.12 g).

NMR (DMSO-$d_6$, δ): 1.73–2.20 (4H, m), 2.80 (3H, s), 3.10–3.50 (4H, m), 3.90–4.60 (2H), 5.13 (1H, d, J=5 Hz), 5.90 (1H, dd, J=5 Hz, 8 Hz), 7.0–7.70 (10H+15H+2H), 8.83 (1H, s), 9.67 (1H, d, J=8 Hz)

EXAMPLE 22

The following compounds were obtained according to similar manners to those of Example 9, 10, 20 and 21.

(1) Benzhydryl 7-[2-(2-tritylaminothiazol-4-yl)-2-difluoromethoxyiminoacetamido]-3-(3-methyl-1,2,4-thiadiazol-5-yl)thiomethyl-3-cephem-4-carboxylate (syn isomer)

IR (Nujol): 3250, 1790, 1725, 1690, 1600, 1530 cm$^{-1}$

NMR (DMSO-$d_6$, δ): 2.50 (3H, s), 3.70 (2H, broad s), 4.25, 4.45 (2H, ABq, J=14 Hz), 5.20 (1H, d, J=5 Hz), 5.75 (1H, dd, J=5 Hz, 8 Hz), 6.97 (1H, s), 7.03 (1H, t, J=72 Hz), 7.10–7.70 (10H+15H), 8.90 (1H, s), 9.83 (1H, d, J=8 Hz)

(2) 7-[2-(2-Aminothiazol-4-yl)-2-difluoromethoxyiminoacetamido]-3-(3-methyl-1,2,4-thiadiazol-5-yl)thiomethyl-3-cephem-4-carboxylic acid (syn isomer)

mp: 135°–140° C. (dec.)

IR (Nujol): 3300, 3200, 1775, 1670, 1620, 1530 cm$^{-1}$ (3) 7-[2-(2-Tritylaminothiazol-4-yl)-2-difluoromethoxyiminoacetamido]-3-(4-carboxy-3-hydroxy-1,2-thiazol-5-yl)thiomethyl-3-cephem-4-carboxylic acid (syn isomer)

IR (Nujol): 3200, 1780, 1710, 1670, 1650, 1590, 1525 cm$^{-1}$ (4) 7-[2-(2-Aminothiazol-4-yl)-2-difluoromethoxyiminoacetamido]-3-(4-carboxy-3-hydroxy-1,2-thiazol-5-yl)thiomethyl-3-cephem-4-carboxylic acid (syn isomer)

mp: 180°–185° C. (dec.)

IR (Nujol): 3300, 1760, 1660, 1600, 1530 cm$^{-1}$ (5) 7-[2-(2-Tritylaminothiazol-4-yl)-2-difluoromethoxyiminoacetamido]-3-(5-methyl-1,3,4-thiadiazol-2-yl)thiomethyl-3-cephem-4-carboxylic acid (syn isomer)

IR (Nujol): 3200, 1780, 1680, 1530 cm$^{-1}$ (6) 7-[2-(2-Aminothiazol-4-yl)-2-difluoromethoxyiminoacetamido]-3-(5-methyl-1,3,4-thiadiazol-2-yl)thiomethyl-3-cephem-4-carboxylic acid (syn isomer)

IR (Nujol): 3250, 1770, 1680, 1610, 1530 cm$^{-1}$ (7) 7-[2-(2-Tritylaminothiazol-4-yl)-2-difluoromethoxyiminoacetamido]-3-(3-ethyl-1-pyridiniomethyl)-3-cephem-4-carboxylate (syn isomer)

IR (Nujol): 1780, 1680, 1630, 1590, 1530 cm$^{-1}$ (8) 7-[2-(2-Aminothiazol-4-yl)-2-difluoromethoxyiminoacetamido]-3-(3-ethyl-1-pyridiniomethyl)-3-cephem-4-carboxylate (syn isomer)

IR (Nujol): 3270, 1770, 1670, 1610, 1530 cm$^{-1}$ (9) 7-[2-(2-Aminothiazol-4-yl)-2-difluoromethoxyiminoacetamido]-3-(3-mesyl-1-pyridiniomethyl)-3-cephem-4-carboxylate (syn isomer)

IR (Nujol): 3300, 3160, 1770, 1670, 1610, 1530 cm$^{-1}$

NMR (DMSO-$d_6$, δ): 3.43 (3H, s), 3.25, 3.69 (2H, ABq, J=18 Hz), 5.25 (1H, d, J=5 Hz), 5.39, 5.70 (2H, ABq, J=14 Hz), 5.83 (1H, d, J=5 Hz), 6.89 (1H, t, J=71 Hz), 7.16 (1H, s), 8.20–8.45 (1H, m), 9.0–9.15 (1H, m), 9.20–9.40 (1H, m)

(10) 7-[2-(2-Aminothiazol-4-yl)-2-difluoromethoxyiminoacetamido]-3-(4-mesyl-1-pyridiniomethyl)-3-cephem-4-carboxylate (syn isomer)

NMR (DMSO-$d_6$, δ): 3.23, 3.66 (2H, ABq, J=18 Hz), 3.45 (3H, s), 5.26 (1H, d, J=5 Hz), 5.45, 5.70 (2H, ABq, J=14 Hz), 5.80 (1H, d, J=5 Hz), 6.88 (1H, t, J=71 Hz), 7.16 (1H, s), 8.58 (2H, d, J=6 Hz), 9.35 (2H, d, J=6 Hz)

(11) 7-[2-(2-Aminothiazol-4-yl)-2-difluoromethoxyiminoacetamido]-3-(3-methylthio-1-pyridiniomethyl)-3-cephem-4-carboxylate (syn isomer)

IR (Nujol): 3300, 3200, 1770, 1660, 1610, 1530 cm$^{-1}$

NMR (D$_2$O+DMSO-$d_6$, δ): 2.60 (3H, s), 3.16, 3.60 (2H, ABq, J=18 Hz), 5.16, 5.50 (2H, ABq, J=14 Hz), 5.25 (1H, d, J=5 Hz), 5.80 (1H, d, J=5 Hz), 6.86 (1H, t, J=71 Hz), 7.13 (1H, s), 7.70–8.0 (1H, m), 8.16–8.40 (1H, m), 8.50–8.70 (1H, m), 8.80 (1H, s)

(12) 7-[2-(2-Tritylaminothiazol-4-yl)-2-difluoromethoxyiminoacetamido]-3-(1-methyl-4-pyridiniothiomethyl)-3-cephem-4-carboxylate (syn isomer)

(13) 7-[2-(2-Aminothiazol-4-yl)-2-difluoromethoxyiminoacetamido]-3-(1-methyl-4-pyridiniothiomethyl)-3-cephem-4-carboxylate (syn isomer)

IR (Nujol): 3300, 1765, 1670, 1630, 1600, 1535 cm$^{-1}$

(14) Benzhydryl 7-[2-(2-tritylaminothiazol-4-yl)-2-difluoromethoxyiminoacetamido]-3-(1-methyl-3-pyridiniothiomethyl)-3-cephem-4-carboxylate iodide (syn isomer)

NMR (DMSO-d$_6$, δ): 3.40–3.90 (2H, m), 3.90–4.40 (2H, m), 4.20 (3H, s), 5.25 (1H, d, J=5 Hz), 5.90 (1H, dd, J=5 Hz, 8 Hz), 6.70–7.60 (3H+25H), 7.70–8.0 (1H, m), 8.20–8.50 (1H, m), 8.60–8.83 (1H, m), 8.97 (1H, s), 9.83 (1H, d, J=8 Hz)

(15) 7-[2-(2-Aminothiazol-4-yl)-2-difluoromethoxyiminoacetamido]-3-(1-methyl-3-pyridiniothiomethyl)-3-cephem-4-carboxylate (syn isomer)

IR (Nujol): 3300, 3180, 1760, 1670, 1600, 1530 cm$^{-1}$

(16) Benzhydryl 7-[2-(2-tritylaminothiazol-4-yl)-2-difluoromethoxyiminoacetamido]-3-(1-methyl-1-pyrrolidiniomethyl)-3-cephem-4-carboxylate trifluoroacetate (syn isomer)

NMR (DMSO-d$_6$, δ): 1.70–2.20 (4H), 2.70 (3H, s), 3.0–4.0 (2H+4H), 4.10, 4.50 (2H), 5.33 (1H, d, J=5 Hz), 5.87 (1H, dd, J=5 Hz, 8 Hz), 7.0–7.70 (10H+15H+2H), 8.93 (1H, s), 9.90 (1H, d, J=8 Hz)

(17) 7-[2-(2-Aminothiazol-4-yl)-2-difluoromethoxyiminoacetamido]-3-(1-methyl-1-pyrrolidiniomethyl)-3-cephem-4-carboxylate (syn isomer)

IR (Nujol): 3300, 3180, 1770, 1670, 1610, 1535 cm$^{-1}$

EXAMPLE 23

A solution of benzhydryl 7-[2-(2-tritylaminothiazol-4-yl)-2-difluoromethoxyiminoacetamido]-3-[(E)-2-(3-pyridylthio)vinyl]-3-cephem-4-carboxylate (syn isomer) (1.74 g), N,N-dimethylformamide (17 ml) and methyl iodide (2.56 g) was stirred for 6.0 hours at room temperature and poured into diisopropyl ether (170 ml). The resultant precipitates were collected by filtration and washed with diisopropyl ether to give benzhydryl 7-[2-(2-tritylaminothiazol-4-yl)-2-difluoromethoxyiminoacetamido]-3-[(E)-2-(1-methyl-3-pyridiniothio)vinyl]-3-cephem-4-carboxylate iodide (syn isomer) (1.98 g).

NMR (DMSO-d$_6$, δ): 3.70, 4.0 (2H, ABq, J=18 Hz), 4.30 (3H, s), 5.27 (1H, d, J=5 Hz), 5.80 (1H, dd, J=5 Hz, 8 Hz), 6.47 (1H, d, J=16 Hz), 6.90–7.60 (4H+25H), 7.90–9.10 (4H, m), 9 92 (1H, d, J=8 Hz)

EXAMPLE 24

The following compound was obtained according to a similar manner to that of Example 23.

Benzhydryl 7-[2-(2-tritylaminothiazol-4-yl)-2-difluoromethoxyiminoacetamido]-3-(1-methyl-3-pyridiniothiomethyl)-3-cephem-4-carboxylate iodide (syn isomer)

NMR (DMSO-d$_6$, δ): 3.40–3.90 (2H, m), 3.90–4.40 (2H, m), 4.20 (3H, s), 5.25 (1H, d, J=5 Hz), 5.90 (1H, dd, J=5 Hz, 8 Hz), 6.70–7.60 (3H+25H), 7.70–8.0 (1H, m), 8.20–8.50 (1H, m), 8.60–8.83 (1H, m), 8.97 (1H, s), 9.83 (1H, d, J=8 Hz)

EXAMPLE 25

A mixture of benzhydryl 7-[2-(2-tritylaminothiazol-4-yl)-2-difluoromethoxyiminoacetamido]-3-chloromethyl-3-cephem-4-carboxylate (syn isomer) (35 g), m-chloroperbenzoic acid (8.64 g) and ethyl acetate (300 ml) was stirred for 30 minutes at 0° to 5° C. and then, water (300 ml), sodium bisulfite and sodium bicarbonate were added thereto. The organic layer was separated, washed with an aqueous solution of sodium chloride, dried over magnesium sulfate and evaporated. The residue was triturated with diisopropyl ether to give benzhydryl 7-[2-(2-tritylaminothiazol-4-yl)-2-difluoromethoxyiminoacetamido]-3-chloromethyl-3-cephem-4-carboxylate-1-oxide (syn isomer) (29.93 g).

NMR (DMSO-d$_6$, δ): 3.30, 3.73 (2H, ABq, J=18 Hz), 4.45 (2H, broad s), 5.27 (1H, d, J=5 Hz), 5.78 (1H, dd, J=5 Hz, 8 Hz), 6.90–7.60 (3H+25H), 8.90 (1H, broad s), 9.88 (1H, d, J=8 Hz)

EXAMPLE 26

The following compounds were obtained according to a similar manner to that of Example 25.

(1) Benzhydryl 7-[2-(2-tritylaminothiazol-4-yl)-2-difluoromethoxyiminoacetamido]-3-iodomethyl-3-cephem-4-carboxylate-1-oxide (syn isomer)

NMR (DMSO-d$_6$, δ): 3.0–4.0 (2H, m), 4.40 (2H, broad s), 5.05 (1H, d, J=5 Hz), 5.80 (1H, d, J=5 Hz, 8 Hz), 6.70–7.80 (3H+25H), 8.85 (1H, broad s), 9.53 (1H, d, J=8 Hz)

(2) Benzhydryl 7-[2-(2-tritylaninothiazol-4-yl)-2-difluoromethoxyiminoacetamido]-3-(1-methyl-1-pyrrolidiniomethyl)-3-cephem-4-carboxylate-1-oxide iodide (syn isomer)

NMR (DMSO-d$_6$, δ): 1.73–2.20 (4H, m), 2.80 (3H, s), 3.10–3.50 (4H, m), 3.90–4.60 (2H), 5.13 (1H, d, J=5 Hz), 5.90 (1H, dd, J=5 Hz, 8 Hz), 7.0–7.70 (10H+15H+2H), 8.83 (1H, s), 9.67 (1H, d, J=8 Hz)

EXAMPLE 27

A mixture of benzhydryl 7-[2-(2-tritylaminothiazol-4-yl)-2-difluoromethoxyiminoacetamido]-3-chloromethyl-3-cephem-4-carboxylate-1-oxide (syn isomer) (29 g), sodium iodide (14.6 g) and acetone (300 ml) was stirred for 2.0 hours at 0°–5° C. and evaporated. To the residue were added ethyl acetate (400 ml) and water (300 ml), and the organic layer was separated, dried and evaporated. The residue was subjected to column chromatography on silica gel (600 g) and the elution was carried out with a mixture of chloroform and ethyl acetate (15:1). The fractions containing the object compound were combined and evaporated. The residue was triturated with diisopropyl ether to give benzhydryl 7-[2-(2-tritylaminothiazol-4-yl)-2-difluoromethoxyiminoacetamido]-3-iodomethyl-3-cephem-4-carboxylate-1-oxide (syn isomer) (13.57 g).

NMR (DMSO-d$_6$, δ): 3.0–4.0 (2H, m), 4.40 (2H, broad s), 5.05 (1H, d, J=5 Hz), 5.80 (1H, d, J=5 Hz, 8 Hz), 6.70–7.80 (3H+25H), 8.85 (1H, broad s), 9.53 (1H, d, J=8 Hz)

EXAMPLE 28

A mixture of benzhydryl 7-[2-(2-tritylaminothiazol-4-yl)-2-difluoromethoxyiminoacetamido]-3-(1-methyl-1-pyrrolidiniomethyl)-3-cephem-4-carboxylate-1-oxide iodide (syn isomer) (1.45 g) and acetonitrile (14 ml) was stirred under cooling in an ice-bath, and N,N-dimethylaniline (490 mg) and phosphorus trichloride (555 mg) were added thereto. The mixture was stirred for one hour under cooling in an ice-bath, and then diisopropyl ether was added to the reaction mixture. The separated oil was triturated with diisopropyl ether to give benzhydryl 7-[2-(2-tritylaminothiazol-4-yl)-2-difluoromethoxyiminoacetamido]-3-(1-methyl-1-pyrrolidiniomethyl)-3-cephem-4-carboxylate iodide. This compound was dissolved in a solution of tetrahydrofuran (54 ml) and water (3.6 ml). The solution was subjected to column chromatography on Amberlite IRA-400 (CF$_3$COO$^\ominus$ form) and the elution was carried out with a solution of water and tetrahydrofuran (1:15). The fractions containing the object compound were collected and evaporated. The residue was triturated with diisopropyl ether to give benzhydryl 7-[2-(2-tritylaminothiazol-4-yl)-2-difluoromethoxyiminoacetamido]-3-(1-methyl-1-pyrrolidiniomethyl)-3-cephem-4-carboxylate trifluoroacetate (syn isomer) (1.30 g).

NMR (DMSO-$d_6$, δ): 1.70–2.20 (4H), 2.70 (3H, s), 3.0–4.0 (2H +4H), 4.10, 4.50 (2H), 5.33 (1H, d, J=5 Hz), 5.87 (1H, dd, J=5 Hz, 8 Hz), 7.0–7.70 (10H+15H+2H), 8.93 (1H, s), 9.90 (1H, d, J=8 Hz)

EXAMPLE 29

The following compounds were obtained acccrding to a similar manner to that of Example 28.

(1) 7-[2-(2-Aminothiazol-4-yl)-2-difluoromethoxyiminoacetamido]-3-(1,3,4-thiadiazol-2-yl)thiomethyl-3-cephem-4-carboxylic acid (syn isomer)

IR (Nujol): 3300, 1770, 1670, 1530 cm$^{-1}$ (2) Benzhydryl 7-[2-(2-tritylaminothiazol-4-yl)-2-difluoromethoxyiminoacetamido]-3-(4-methyl-5-oxo-6-hydroxy-4,5-dihydro 1,2,4-triazin-3-yl)thiomethyl-3-cephem-4-carboxylate (syn isomer)

IR (Nujol): 1780, 1705, 1670, 1580, 1520 cm$^{-1}$ (3) 7-[2-(2-Aminothiazol-4-yl)-2-difluoromethoxyiminoacetamido]-3-(4-methyl-5-oxo-6-hydroxy-4,5-dihydro-1,2,4-triazin-3-yl)thiomethyl-3-cephem-4-carboxylic acid (syn isomer)

IR (Nujol): 1770, 1690, 1680, 1580, 1520 cm$^{-1}$ (4) 7-[2-(2-Aminothiazol-4-yl)-2-difluoromethoxyiminoacetamido]-3-(1,2,3-thiadiazol-5-yl)thiomethyl-3-cephem-4-carboxylic acid (syn isomer)

IR (Nujol): 3250, 1770, 1670, 1620, 1530 cm$^{-1}$ (5) 7-[2-(2-Tritylaminothiazol-4-yl)-2-difluoromethoxyiminoacetamido]-3-(3-methyl-1-pyridiniomethyl)-3-cephem-4-carboxylate (syn isomer)

IR (Nujol): 3300, 1780, 1670, 1620, 1530 cm$^{-1}$ (6) 7-[2-(2-Aminothiazol-4-yl)-2-difluoromethoxyiminoacetamido]-3-(3-methyl-1-pyridiniomethyl)-3-cephem-4-carboxylate (syn isomer)

IR (Nujol): 3300, 3150, 1770, 1670, 1610, 1530 cm$^{-1}$ (7) 7-[2-(2-Tritylaminothiazol-4-yl)-2-difluoromethoxyiminoacetamido]-3-[1-(2-hydroxyethyl)-1H-tetrazol-5-yl]thiomethyl-3-cephem-4-carboxylic acid (syn isomer)

IR (Nujol): 3230, 1780, 1680, 1530 cm$^{-1}$ (8) 7-[2-(2-Aminothiazol-4-yl)-2-difluoromethoxyiminoacetamido]-3-[1-(2-hydroxyethyl)-1H-tetrazol-5-yl]thiomethyl-3-cephem-4-carboxylic acid (syn isomer)

IR (Nujol): 3300, 1770, 1670, 1620, 1530 cm$^{-1}$ (9) 7-[2-(2-Tritylaminothiazol-4-yl)-2-difluoromethoxyiminoacetamido]-3-(1,2,4-thiadiazol-5-yl)thiomethyl-3-cephem-4-carboxylic acid (syn isomer)

IR (Nujol): 3300, 1780, 1650, 1590, 1530 cm$^{-1}$

(10) 7-[2-(2-Aminothiazol-4-yl)-2-difluoromethoxyiminoacetamido]-3-(1,2,4-thiadiazol-5-yl)thiomethyl-3-cephem-4-carboxylic acid (syn isomer)

IR (Nujol): 3250, 1770, 1670, 1620, 1530 cm$^{-1}$

(11) 7-[2-(2-Tritylaminothiazol-4-yl)-2-difluoromethoxyiminoacetamido]-3-[1-{2-(N,N-dimethylamino)ethyl}-1H-tetrazol-5-yl]thiomethyl-3-cephem-4-carboxylic acid (syn isomer)

IR (Nujol): 3250, 1770, 1660, 1530 cm$^{-1}$

(12) 7-[2-(2-Aminothiazol-4-yl)-2-difluoromethoxyiminoacetamido]-3-[1-{2-(N,N-dimethylamino)ethyl}-1H-tetrazol-5-yl]thiomethyl-3-cephem-4-carboxylic acid (syn isomer)

IR (Nujol): 3300, 1670, 1610, 1530 cm$^{-1}$

(13) Benzhydryl 7-[2-(2-tritylaminothiazol-4-yl)-2-difluoromethoxyiminoacetamido]-3-[(Z)-2-cyanovinylthiomethyl]-3-cephem-4-carboxylate (syn isomer)

IR (Nujol): 3250, 2210, 1780, 1720, 1680, 1520, 1490 cm$^{-1}$

(14) 7-[2-(2-Aminothiazol-4-yl)-2-difluoromethoxyiminoacetamido]-3-[(Z)-2-cyanovinylthiomethyl]-3-cephem-4-carboxylic acid (syn isomer)

mp: 145° to 15° C. (dec.)

IR (Nujol): 3260, 2210, 1770, 1675, 1620, 1560, 1530 cm$^{-1}$

(15) 7-[2-(2-Tritylaminothiazol-4-yl)-2-difluoromethoxyiminoacetamido]-3-(2-methyl-5-oxo-6-hydroxy-2,5-dihydro-1,2,4-triazin-3-yl)thiomethyl-3-cephem-4-carboxylic acid (syn isomer)

mp: 125° to 130° C. (dec )

IR (Nujol): 3200, 1780, 1655, 1590, 1530 cm$^{-1}$

(16) 7-[2-(2-Aminothiazol-4-yl)-2-difluoromethoxyiminoacetamido]-3-(2-methyl-5-oxo-6-hydroxy-2,5-dihydro-1,2,4-triazin-3-yl)thiomethyl-3-cephem-4-carboxylic acid (syn isomer)

mp: 165° to 170° C. (dec.)

IR (Nujol): 3300, 3200, 1780, 1680, 1640, 1530 cm$^{-1}$

(17) 7-[2-(2-Aminothiazol-4-yl)-2-difluoromethoxyiminoacetamido]-3-carbamoyloxymethyl-3-cephem-4-carboxylic acid (syn isomer)

mp: 125° to 130° C. (dec.)

IR (Nujol): 3450, 3350, 3260, 3200, 1770, 1720, 1680, 1650, 1600, 1530 cm$^{-1}$

(18) 7-[2-(2-Tritylaminothiazol-4-yl)-2-difluoromethoxyiminoacetamido]-3-carbamoyloxymethyl-3-cephem-4-carboxylic acid (syn isomer)

mp: 125° to 130° C. (dec.)

IR (Nujol): 3200, 1775, 1710, 1670, 1590, 1520 cm$^{-1}$

(19) 7-[2-(2-Aminothiazol-4-yl)-2-difluoromethoxyiminoacetamido]-3-(tetrazolo[1,5-b]pyridazin-6-yl)thiomethyl-3-cephem-4-carboxylic acid (syn isomer)

mp: 170° to 175° C. (dec.)

IR (Nujol): 3400, 3260, 3200, 1770, 1680, 1660, 1620, 1535 cm$^{-1}$

(20) 7-[2-(2-Tritylaminothiazol-4-yl)-2-difluoromethoxyiminoacetamido]-3-(tetrazolo[1,5-b]pyridazin-6-yl)thiomethyl-3-cephem-4-carboxylic acid (syn isomer)

mp: 130° to 135° C. (dec.)

IR (Nujol): 3200, 1785, 1680, 1595, 1575, 1530 cm$^{-1}$

(21) 7-[2-(2-Aminothiazol-4-yl)-2-difluoromethoxyiminoacetamido]-3-(1-methyl-1H-tetrazol-5-yl)thiomethyl-3-cephem-4-carboxylic acid (syn isomer)

mp: 145° to 150° C. (dec.)

IR (Nujol): 3300, 1770, 1670, 1620, 1530 cm$^{-1}$

(22) 7-[2-(2-Tritylaminothiazol-4-yl)-2-difluoromethoxyiminoacetamido]-3-(1-methyl-1H-tetrazol-5-yl)thiomethyl- 3-cephem-4-carboxylic acid (syn isomer)

mp: 115° to 120° C. (dec.)

IR (Nujol): 3200, 1770, 1660, 1585, 1560, 1515 cm$^{-1}$

(23) 7-[2-(2-Tritylaminothiazol-4-yl)-2-difluoromethoxyiminoacetamido]-3-vinyl-3-cephem-4-carboxylic acid (syn isomer)

mp: 105° to 110° C. (dec.)

IR (Nujol): 3200, 1770, 1680, 1650, 1585, 1565, 1520 cm$^{-1}$

(24) 7-[2-(2-Aminothiazol-4-yl)-2-difluoromethoxyiminoacetamido]-3-vinyl-3-cephem-4-carboxylic acid (syn isomer)

mp: 190° to 195° C. (dec.)

IR (Nujol): 3420, 3320, 3250, 1770, 1670, 1615, 1530 cm$^{-1}$

(25) 7-[2-(2-Tritylaminothiazol-4-yl)-2-difluoromethoxyiminoacetamido]-3-(1,2,5-thiadiazol-3-yl)thiomethyl-3-cephem-4-carboxylic acid (syn isomer)

IR (Nujol): 3200, 1775, 1680, 1520 cm$^{-1}$

(26) 7-[2-(2-Aminothiazol-4-yl)-2-difluoromethoxyiminoacetamido]-3-(1,2,5-thiadiazol-3-yl)thiomethyl-3-cephem-4-carboxylic acid (syn isomer)

mp: 120° to 125° C. (dec.)

IR (Nujol): 3300, 3180, 1770, 1670, 1620, 1530 cm$^{-1}$

(27) 7-[2-(2-Tritylaminothiazol-4-yl)-2-difluoromethoxyiminoacetamido]-3-(1,3,4-thiadiazol-2-yl)thiomethyl-3-cephem-4-carboxylic acid (syn isomer)

IR (Nujol): 3250, 1780, 1680, 1530 cm$^{-1}$

(28) Benzhydryl 7-[2-(2-tritylaminothiazol-4-yl)-2-difluoromethoxyiminoacetamido]-3-chloromethyl-3-cephem-4-carboxylate (syn isomer)

IR (Nujol): 1780, 1720, 1670, 1590, 1520 cm$^{-1}$

(29) 7-[2-(2-Tritylaminothiazol-4-yl)-2-difluoromethoxyiminoacetamido]-3-(1,2,3-thiadiazol-5-yl)thiomethyl-3-cephem-4-carboxylic acid (syn isomer)

IR (Nujol): 3200, 1780, 1680, 1520 cm$^{-1}$

(30) Benzhydryl 7-[2-(2-tritylaminothiazol-4-yl)-2-difluoromethoxyiminoacetamido]-3-(3-methyl-1,2,4-thiadiazol-5-yl)thiomethyl-3-cephem-4-carboxylate (syn isomer)

IR (Nujol): 3250, 1790, 1725, 1690, 1600, 1530 cm$^{-1}$

(31) 7-[2-(2-Aminothiazol-4-yl)-2-difluoromethoxyiminoacetamido]-3-(3-methyl-1,2,4-thiadiazol-5-yl)thiomethyl-3-cephem-4-carboxylic acid (syn isomer)

mp: 135°–140° C. (dec.)

IR (Nujol): 3300, 3200, 1775, 1670, 1620, 1530 cm$^{-1}$

(32) 7-[2-(2-Trithylaminothiazol-4-yl)-2-difluoromethoxyiminoacetamido]-3-(4-carboxy-3-hydroxy-1,2-thiazol-5-yl)thiomethyl-3-cephem-4-carboxylic acid (syn isomer)

IR (Nujol): 3200, 1780, 1710, 1670, 1650, 1590, 1525 cm$^{-1}$

(33) 7-[2-(2-Aminothiazol-4-yl)-2-difluoromethoxyiminoacetamido]-3-(4-carboxy-3-hydroxy-1,2-thiazol-5-yl)thiomethyl-3-cephem-4-carboxylic acid (syn isomer)

mp: 180°–185° C. (dec.)

IR (Nujol): 3300, 1760, 1660, 1600, 1530 cm$^{-1}$

(34) 7-[2-(2-Tritylaminothiazol-4-yl)-2-difluoromethoxyiminoacetamido]-3-(5-methyl-1,3,4-thiadiazol-2-yl)thiomethyl-3-cephem-4-carboxylic acid (syn isomer)

IR (Nujol): 3200, 1780, 1680, 1530 cm$^{-1}$

(35) 7-[2-(2-Aminothiazol-4-yl)-2-difluoromethoxyiminoacetamido]-3-(5-methyl-1,3,4-thiadiazol-2-yl)thiomethyl-3-cephem-4-carboxylic acid (syn isomer)

IR (Nujol): 3250, 1770, 1680, 1610, 1530 cm$^{-1}$

(36) 7-[2-(2-Tritylaminothiazol-4-yl)-2-difluoromethoxyiminoacetamido]-3-cephem-4-carboxylic acid (syn isomer)

IR (Nujol): 3200, 1780, 1720 (s), 1680, 1630, 1590, 1530 cm$^{-1}$

(37) 7-[2-(2-Aminothiazol-4-yl)-2-difluoromethoxyiminoacetamido]-3-cephem-4-carboxylic acid (syn isomer)

NMR (DMSO-d$_6$, δ): 3.62 (2H, m), 5.12 (1H, d, J=5 Hz), 5.85 (1H, dd, J=5 Hz, 8 Hz), 6.47 (1H, t, J=2 Hz), 6.98 (1H, s), 7.09 (1H, t, J=72 Hz), 7.30 (2H, broad s), 9.90 (1H, d, J=8 Hz)

(38) 7-[2-(2-Tritylaminothiazol-4-yl)-2-difluoromethoxyiminoacetamido]-3-(3-ethyl-1-pyridiniomethyl)-3-cephem-4-carboxylate (syn isomer)

IR (Nujol): 1780, 1680, 1630, 1590, 1530 cm$^{-1}$

(39) 7-[2-(2-Aminothiazol-4-yl)-2-difluoromethoxyiminoacetamido]-3-(3-ethyl-1-pyridiniomethyl)-3-cephem-4-carboxylate (syn isomer)

IR (Nujol): 3270, 1770, 1670, 1610, 1530 cm$^{-1}$

(40) 7-[2-(2-Aminothiazol-4-yl)-2-difluoromethoxyiminoacetamido]-3-(4-methoxy-1-pyridiniomethyl)-3-cephem-4-carboxylate (syn isomer)

IR (Nujol): 3300, 3150, 1770, 1670, 1635, 1610, 1560, 1515 cm$^{-1}$

(41) 7-[2-(2-Aminothiazol-4-yl)-2-difluoromethoxyiminoacetamido]-3-(3-mesyl-1-pyridiniomethyl)-3-cephem-4-carboxylate (syn isomer)

IR (Nujol): 3300, 3160, 1770, 1670, 1610, 1530 cm$^{-1}$

(42) 7-[2-(2-Aminothiazol-4-yl)-2-difluoromethoxyiminoacetamido]-3-(4-mesyl-1-pyridiniomethyl)-3-cephem-4-carboxylate (syn isomer)

NMR (DMSO-d$_6$, δ): 3.23, 3.66 (2H, ABq, J=18 Hz), 3.45 (3H, s), 5.26 (1H, d, J=5 Hz), 5.45, 5.70 (2H, ABq, J=14 Hz), 5.80 (1H, d, J=5 Hz), 6.88 (1H, t, J=71 Hz), 7.16 (1H, s), 8.58 (2H, d, J=6 Hz), 9.35 (2H, d, J=6 Hz)

(43) 7-[2-(2-Aminothiazol-4-yl)-2-difluoromethoxyiminoacetamido]-3-(3-methylthio-1-pyridiniomethyl)-3-cephem-4-carboxylate (syn isomer)

IR (Nujol): 3300, 3200, 1770, 1660, 1610, 1530 cm$^{-1}$

(44) 7-[2-(2-Tritylaminothiazol-4-yl)-2-difluoromethoxyiminoacetamido]-3-(1-methyl-4-pyridiniothiomethyl)-3-cephem-4-carboxylate (syn isomer)

(45) 7-[2-(2-Aminothiazol-4-yl)-2-difluoromethoxyiminoacetamido]-3-(1-methyl-4-pyridiniothiomethyl)-3-cephem-4-carboxylate (syn isomer)

IR (Nujol): 3300, 1765, 1670, 1630, 1600, 1535 cm$^{-1}$

(46) Benzhydryl 7-[2-(2-tritylaminothiazol-4-yl)-2-difluoromethoxyiminoacetamido]-3-[(E)-2-(3-pyridylthio)vinyl]-3-cephem-4-carboxylate (syn isomer)

NMR (DMSO-d$_6$, δ): 3.67–4.0 (2H, m), 5.25 (1H, d, J=5 Hz), 5.77 (1H, dd, J=5 Hz, 8 Hz), 6.53 (1H, d, J=16 Hz), 6.90–7.70 (4H+25H), 7.70–9.0 (4H, m), 9.90 (1H, d, J=8 Hz)

(47) Benzhydryl 7-[2-(2-Tritylaminothiazol-4-yl)-2difluoromethoxyiminoacetamido]-3-[(E)-2-(1-methyl-3-pyridiniothio)vinyl]-3-cephem-4-carboxylate iodide (syn isomer)

NMR (DMSO-d$_6$, δ): 3.70, 4.0 (2H, ABq, J=18 Hz), 4.30 (3H, s), 5.27 (1H, d, J=5 Hz), 5.80 (1H, dd, J=5 Hz, 8 Hz), 6.47 (1H, d, J=16 Hz), 6.90–7.60 (4H+25H), 7.90–9.10 (4H, m), 9.92 (1H, d, J=8 Hz)

(48) 7-[2-(2-Aminothiazol-4-yl)-2-difluoromethoxyiminoacetamido]-3-[(E)-2-(1-methyl-3-pyridiniothio)vinyl]-3-cephem-4-carboxylate (syn isomer)

IR (Nujol): 3300, 3170, 1760, 1665, 1600, 1530, 1490 cm$^{-1}$

(49) Benzhydryl 7-[2-(2-tritylaminothiazol-4-yl)-2-difluoromethoxyiminoacetamido]-3-(1-methyl-3-pyridiniothiomethyl)-3-cephem-4-carboxylate iodide (syn isomer)

NMR (DMSO-d$_6$, δ): 3.40–3.90 (2H, m), 3.90–4.40 (2H, m), 4.20 (3H, s), 5.25 (1H, d, J=5 Hz), 5.90 (1H, dd, J=5 Hz, 8 Hz), 6.70–7.60 (3H+25H), 7.70–8.0 (1H, m), 8.20–8.50 (1H, m), 8.60–8.83 (1H, m), 8.97 (1 H, s), 9.83 (1H, d, J=8 Hz)

(50) 7-[2-(2-Aminothiazol-4-yl)-2-difluoromethoxyiminoacetamido]-3-(1-methyl-3-pyridiniothiomethyl)-3-cephem-4-carboxylate (syn isomer)

IR (Nujol): 3300, 3180, 1760, 1670, 1600, 1530 cm$^{-1}$

(51) 7-[2-(2-Aminothiazol-4-yl)-2-difluoromethoxyiminoacetamido]-3-(1-methyl-1-pyrrolidiniomethyl)-3-cephem-4-carboxylate (syn isomer)

IR (Nujol): 3300, 3180, 1770, 1670, 1610, 1535 cm$^{-1}$

(52) Sodium 7-[2-(2-aminothiazol-4-yl)-2-difluoromethoxyiminoacetamido]-3-hydroxymethyl-3-cephem-4-carboxylate (syn isomer)

IR (Nujol): 3300, 1750, 1665, 1600, 1525 cm$^{-1}$

EXAMPLE 30

The following compounds were obtained according to similar manners to those of aforementioned Examples.

(1) 7-[2-(2-Tritylaminothiazol-4-yl)-2-difluoromethoxyiminoacetamido]-3-(2-methyl-1-pyridiniomethyl)-3-cephem-4-carboxylate (syn isomer)

NMR (DMSO-d$_6$, δ): 2.73 (3H, s), 3.43 (2H, broad s), 5.20 (1H, d, J=5 Hz), 5.63 (2H, broad s), 5.87 (1H, dd, J=5 Hz, 8 Hz), 6.90 (1H, t, J=72 Hz), 7.05–7.60 (15H, m), 7.70–8.27 (2H, m), 8.47 (1H, dd, J=6 Hz, 8 Hz), 8.92 (1H, broad s), 8.97 (1H, d, J=6 Hz), 9.88 (1H, d, J=8 Hz)

(2) 7-[2-(2-Aminothiazol-4-yl)-2-difluoromethoxyiminoacetamido]-3-(2-methyl-1-pyridiniomethyl)-3-cephem-4-carboxylate (syn isomer)

IR (Nujol): 3250, 1770, 1660, 1610, 1530 cm$^{-1}$

NMR (D$_2$O-NaHCO$_3$, δ): 2.82 (3H, s), 3.17, 3.50 (2H, ABq, J=18 Hz), 5.25 (1H, d, J=5 Hz), 5.31, 5.57 (2H, ABq, J=14 Hz), 5.85 (1H, d, J=5 Hz), 6.90 (1H, t, J=72 Hz), 7.15 (1H, s), 7.75–7.98 (2H, m), 8.33 (1H, dd, J=6 Hz, 8 Hz), 8.70 (1H, d, J=6 Hz)

(3) 7-[2-(2-Aminothiazol-4-yl)-2-difluoromethoxyiminoacetamido]-3-[2-(2-hydroxyethyl)-1-pyridiniomethyl]-3-cephem-4-carboxylate (syn isomer)

NMR (D$_2$O-NaHCO$_3$, δ): 3.14, 3.53 (2H, ABq, J=18 Hz), 3.38 (2H, t, J=6 Hz), 4.03 (2H, t, J=6 Hz), 5.25 (1H, d, J=5 Hz), 5.42, 5.62 (2H, ABq, J=14 Hz), 5.85 (1H, d, J=5 Hz), 6.88 (1H, t, J=72 Hz), 7.20 (1H, s), 7.77–8.10 (2H, m), 8.43 (1H, dd, J=6 Hz, 8 Hz), 8.78 (1H, d, J=6 Hz)

(4) 7-[2-(2-Tritylaminothiazol-4-yl)-2-difluoromethoxyiminoacetamido]-3-(2,3-dimethyl-1-pyridiniomethyl)-3-cephem-4-carboxylate (syn isomer)

IR (Nujol): 3200, 1780, 1670, 1590, 1570, 1620 cm$^{-1}$

NMR (DMSO-d$_6$, δ): 2.37 (3H, s), 2.60 (3H, s), 3.30 (2H, broad s), 5.12 (1H, d, J=5 Hz), 5.62 (2H, broad s), 5.70 (1H, dd, J=5 Hz, 8 Hz), 7.00 (1H, t, J=72 Hz), 7.03 (1H, s), 6.50–7.60 (15H, m), 7.77 (1H, m), 8.37 (1H, d, J=8 Hz), 8.75 (1H, d, J=6 Hz), 9.82 (1H, d, J=8 Hz)

(5) 7-[2-(2-Aminothiazol-4-yl)-2-difluoromethoxyiminoacetamido]-3-(2,3-dimethyl-1-pyridiniomethyl)-3-cephem-4-carboxylate (syn isomer)

IR (Nujol): 3300, 1770, 1660, 1600, 1530 cm$^{-1}$

NMR (D$_2$O, δ): 2.47 (3H, s), 2.71 (3H, s), 3.12, 3.40 (2H, ABq, J=18 Hz), 5.22 (1H, d, J=5 Hz), 5.32, 5.63 (2H, ABq, J=14 Hz), 5.85 (1H, d, J=5 Hz), 6.87 (1H, t, J=72 Hz), 7.12 (1H, s), 7.66 (1H, dd, J=6 Hz, 8 Hz), 8.18 (1H, d, J=8 Hz), 8.55 (1H, d, J=6 Hz)

(6) 7-[2-(2-Aminothiazol-4-yl)-2-difluoromethoxyiminoacetamido]-3-(1,2,3,6-tetrahydropyridin-1-ylmethyl)-3-cephem-4-carboxylic acid (syn isomer)

IR (Nujol): 3300, 1760, 1610, 1520 cm$^{-1}$

NMR (D$_2$O-NaHCO$_3$, δ): 2.40 (2H, m), 3.25 (2H, t, J=7 Hz), 3.40–3.65 (4H, m), 3.77, 4.00 (2H, ABq, J=14 Hz), 5.25 (1H, d, J=5 Hz), 5.82 (1H, d, J=5 Hz), 5.50–6.10 (2H, m), 6.90 (1H, t, J=72 Hz), 7.22 (1H, s)

(7) Benzhydryl 7-[2-(2-tritylaminothiazol-4-yl)-2-difluoromethoxyiminoacetamido]-3-(1,2,3,4-tetrahydroisoquinolin-2-ylmethyl)-3-cephem-4-carboxylate-1-oxide (syn isomer)

IR (Nujol): 3270, 1780, 1720, 1670, 1590, 1520 cm$^{-1}$

NMR (DMSO-d$_6$, δ): 3.30 (8H, m), 3.48, 3.82 (2H, ABq, J=14 Hz), 5.07 (1H, d, J=5 Hz), 5.80 (1H, dd, J=5 Hz, 8 Hz), 6.97 (1H, s), 7.03 (1H, t, J=72 Hz), 7.05 (1H, s), 7.32 (25H, m), 8.85 (1H, broad s), 9.47 (1H, d, J=8 Hz)

(8) Benzhydryl 7-[2-(2-tritylaminothiazol-4-yl)-2-difluoromethoxyiminoacetamido]-3-(1,2,3,4-tetrahydroisoquinolin-2-ylmethyl)-3-cephem-4-carboxylate (syn isomer)

IR (Nujol): 3325, 1785, 1710, 1680, 1520 cm$^{-1}$

NMR (DMSO-d$_6$, δ): 3.10 (2H, m), 3.60 (4H, m), 4.03 (4H, m), 5.33 (1H, d, J=5 Hz), 5.83 (1H, dd, J=5 Hz, 8 Hz), 6.97 (1H, s), 7.02 (1H, s), 7.10 (1H, t, J=72 Hz), 7.37 (29H, m), 8.95 (1H, broad s), 9.92 (1H, d, J=8 Hz)

(9) 7-[2-(2-Aminothiazol-4-yl)-2-difluoromethoxyiminoacetamido]-3-(1,2,3,4-tetrahydroisoquinolin-2-ylmethyl)-3-cephem-4-carboxylic acid (syn isomer)

IR (Nujol): 3300, 1770, 1670, 1600, 1530 cm$^{-1}$

NMR (DMSO-d$_6$, δ): 2.95 (4H, m), 3.50, 3.73 (2H, ABq, J=18 Hz), 3.88 (2H, m), 4.20 (2H, m), 5.21 (1H, d, J=5 Hz), 5.78 (1H, dd, J=5 Hz, 8 Hz), 7.02 (1H, s), 7.14 (1H, t, J=72 Hz), 7.18 (4H, m), 7.35 (2H, broad s), 9.85 (1H, d, J=8 Hz)

What we claim is:

1. A compound of the formula:

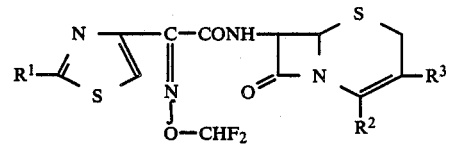

wherein

R$^1$ is amino or a protected amino group,

R$^2$ is carboxy or a protected carboxy group and

R$^3$ is thiadiazolylthiomethyl or thiadiazolylthiomethyl substituted with lower alkyl, and pharmaceutically acceptable salts thereof.

2. Syn isomer of a compound of claim 1.

3. A compound of claim 2, wherein

R$^1$ is amino or ar(lower)alkylamino, and

R$^2$ is carboxy or esterified carboxy.

4. A compound of claim 3, wherein

R$^1$ is amino or triphenyl)lower)alkylamino,

R$^2$ is carboxy or ar(lower)alkoxycarbonyl, and

R$^3$ is 1,3,4-thiadiazolylthiomethyl, 1,2,4-thiadiazolylthiomethyl or 1,2,4-thiadiazolylthiomethyl substituted with lower alkyl.

5. A compound of claim 4, wherein

R$^1$ is amino,

R$^2$ is carboxy, and

R$^3$ is 1,2,4-thiadiazolylthiomethyl.

6. A compound of claim 5, which is 7-[2-(2-aminothiazol-4-yl)-2-difluoromethoxyimino-acetamido-3-(1,2,4-thiadiazol-5-yl)thiomethyl-3-cephem-4-carboxylic acid (syn isomer).

7. An antimicrobial pharmaceutical composition comprising an antimicrobially effective amount of a compound of claim 1 or pharmaceutically acceptable salt thereof in association with a pharmaceutically acceptable, substantially non-toxic carrier or excipient.

8. A method of treating infectious disease in a human being or animal which comprises administering an antimicrobially effective amount of a compound of claim 1 or pharmaceutically acceptable salt thereof.

* * * * *